(12) United States Patent
Duffy et al.

(10) Patent No.: US 7,196,106 B2
(45) Date of Patent: Mar. 27, 2007

(54) CYANOTHIOPHENE DERIVATIVES, COMPOSITIONS CONTAINING SUCH COMPOUNDS AND METHODS OF USE

(75) Inventors: Joseph L. Duffy, Cranford, NJ (US); Elizabeth Louise Campbell, North Brunswick, NJ (US); Brian A. Kirk, Basking Ridge, NJ (US); Rui Liang, East Brunswick, NJ (US); James R. Tata, Westfield, NJ (US); Kevin T. Chapman, Scotch Plains, NJ (US); Zenon Konteatis, Chatham Township, NJ (US)

(73) Assignee: Merck & Co., Inc, Rahway, NJ (US)

( * ) Notice: Subject to any disclaimer, the term of this patent is extended or adjusted under 35 U.S.C. 154(b) by 117 days.

(21) Appl. No.: 10/701,186

(22) Filed: Nov. 4, 2003

(65) Prior Publication Data
US 2004/0097552 A1    May 20, 2004

Related U.S. Application Data

(60) Provisional application No. 60/423,812, filed on Nov. 5, 2002.

(51) Int. Cl.
*A61K 31/4245* (2006.01)
*A61K 31/381* (2006.01)
*C07D 333/38* (2006.01)
*C07D 413/04* (2006.01)

(52) U.S. Cl. .................. 514/364; 514/444; 514/438; 514/336; 514/374; 514/340; 514/252.13; 514/253.11; 544/364; 544/374; 546/269.4; 548/131; 548/235

(58) Field of Classification Search .............. 549/61, 549/59; 548/131, 235; 546/269.4; 544/374, 544/364; 514/444, 438, 364, 336, 374, 340, 514/252.13, 253.11
See application file for complete search history.

(56) References Cited

U.S. PATENT DOCUMENTS

| 3,953,468 | A | | 4/1976 | Wechter et al. |
| 4,359,474 | A | | 11/1982 | Anderson et al. |
| 4,567,196 | A | | 1/1986 | Wierzbicki |
| 4,608,384 | A | | 8/1986 | Wierzbicki et al. |
| 4,831,013 | A | | 5/1989 | Francis |
| 5,422,335 | A | * | 6/1995 | Hagen et al. ............... 504/104 |
| 5,776,954 | A | | 7/1998 | de Laszlo et al. |
| 6,048,880 | A | * | 4/2000 | Kawai et al. ............... 514/336 |
| 2004/0122016 | A1 | * | 6/2004 | Cao et al. ............. 514/252.05 |

FOREIGN PATENT DOCUMENTS

| DE | 36 24 304 A1 | 1/1986 |
| DE | 35 07 421 A1 | 9/1986 |
| DE | 35 29 247 A1 | 11/1986 |
| DE | 41 19 767 A1 | 2/2002 |
| EP | 0 193 885 A1 | 9/1986 |
| EP | 0 193 885 B1 | 9/1986 |
| EP | 0 202 538 A1 | 11/1986 |
| EP | 0 202 538 B1 | 11/1986 |
| EP | 0 217 748 A2 | 4/1987 |
| EP | 0 217 748 B1 | 4/1987 |
| EP | 0 253 259 A2 | 1/1988 |
| EP | 0 253 259 A3 | 1/1988 |
| EP | 0 263 071 A1 | 4/1988 |
| EP | 0 263 071 B1 | 4/1988 |
| FR | 2 564 467 | 11/1985 |
| FR | 2 565 981 | 12/1985 |
| JP | 2002-50169 | 2/2002 |
| WO | WO 97/16442 | 5/1997 |
| WO | WO 98/04528 A2 | 2/1998 |
| WO | WO 98/04528 A3 | 2/1998 |
| WO | WO 98/21957 | 5/1998 |
| WO | WO 99/22108 | 5/1998 |
| WO | WO 99/22109 | 5/1998 |
| WO | WO 99/32448 | 7/1998 |
| WO | WO 99/01423 | 1/1999 |
| WO | WO 99/32448 | 7/1999 |
| WO | WO 99/46267 | 9/1999 |
| WO | WO 00/39088 | 7/2000 |
| WO | WO 00/69810 | 11/2000 |
| WO | WO 01/32632 A2 | 5/2001 |
| WO | WO 01/32632 A3 | 5/2001 |
| WO | WO 01/36415 | 5/2001 |
| WO | WO 01/40223 A2 | 6/2001 |
| WO | WO 01/40223 A3 | 6/2001 |
| WO | WO 01/44226 | 6/2001 |
| WO | WO 01/46165 | 6/2001 |
| WO | WO 01/58890 | 8/2001 |
| WO | WO 02/18335 | 3/2002 |

OTHER PUBLICATIONS

Al-Omron et al., Journal of Heterocyclic Chemistry (Sep.-Oct. 2002), 39(5), pp. 877-883.*

(Continued)

*Primary Examiner*—Laura L. Stockton
(74) *Attorney, Agent, or Firm*—Richard C. Billups; Melvin Winokur

(57) ABSTRACT

The present invention addresses substituted cyanothiophene derivatives of the formula I:

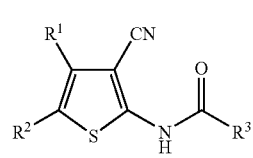

as well as compositions containing such compounds and methods of treatment. The compounds in the present invention are glucagon antagonists. The compounds block the action of glucagon at its receptor and thereby decrease the levels of plasma glucose providing a treatment of diabetes.

9 Claims, No Drawings

OTHER PUBLICATIONS

Guillon, Jean, et al., "Synthesis of new pyrrolo[1,2-α]quinoxalines: potential non-peptide glucagon receptor antagonist", *Eur. J. Med. Chem*, 33, pp. 293-308 (1998).

Petersen, K. F., et al., "Effects of a novel glucagon receptor antagonist (Bay 27-9955) on glucagon-stimulated glucose production in humans", *Diabetologia*, 44, pp. 2018-2024 (2001).

Ladouceur, Gaetan, H., et al., "Discovery of 5-Hydroxyalkyl-4-phenylpyridines as a New Class of Glucagon Receptor Antagonists", *Bioorganic & Medicinal Chemistry Letters*, 12, pp. 461-464 (2002).

Cascieri, Margaret, A., Characterization of a Novel, Non-peptidyl Antagonist of the Human Glucagon Receptor, *The Journal of Biological Chemistry*, vol. 274, Issue of Mar. 26, pp. 8694-8697 (1999).

de Laszlo, Stephen, E., "Potent, Orally Absorbed Glucagon Receptor Antagonists", *Bioorganic & Medicinal Chemistry Letters*, 9, pp. 641-646 (1999).

Madsen, Peter, et al., "Discovery and Structure-Activity Relationship of the First Non-Peptide Competitive Human glucagon Receptor Antagonists", *J. Med Chem*, 41, pp. 5150-5157 (1998).

Ling, Anthony, et al., "Identification of Alkylidene Hydrazides as Glucagon Receptor Antagonists", *J. Med. Chem*, 44, pp. 3141-3149 (2001).

Ling, Anthony, et al., "Human Glucagon Receptor Antagonists Based on Alkylidine Hydrazides", *Bioorganic & Medicinal Chemistry Letters*, 12, pp. 663-666 (2002).

Collins, Judith, L., "CP-99,711: A Non-Peptide Glucagon Receptor Antagonist", Bioorganic & Medicinal Chemistry Letters, vol. 2, No. 9, pp. 915-918 (1992).

Parker, Janice, C., "Effects of Skyrin, a Receptor-Selective Glucagon Antagonist, in Rat and human Hepatocytes", *Diabetes*, vol. 49, pp. 2079-2086 (Dec. 2000).

Connell, Richard, D., "Glucagon antagonists for the treatment of Type 2 diabetes", *Expert Opinion on Therapeutic patents*, 9(6), pp. 701-709 (1999).

Madsen, P., et al., "Advances in Non-Peptide Glucagon Receptor Antagonists", Current Pharmaceutical Design, 5, pp. 683-691 (1999).

* cited by examiner

CYANOTHIOPHENE DERIVATIVES, COMPOSITIONS CONTAINING SUCH COMPOUNDS AND METHODS OF USE

CROSS-REFERENCE TO RELATED APPLICATIONS

The present invention is related to U.S. provisional application Ser. No. 60/423,812, filed Nov. 5, 2002, the contents of which are hereby incorporated by reference.

BACKGROUND OF THE INVENTION

The present invention relates to substituted cyanothiophene derivatives, compositions containing such compounds and methods of treating type 2 diabetes mellitus.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level ≧126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure ≧130/80 mmHg in a resting state), nephropathy, neuropathy and retinopathy.

Patients having type 2 diabetes mellitus characteristically exhibit elevated plasma insulin levels compared with non-diabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by α-cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

A compound represented by formula I:

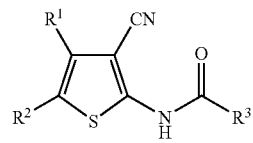

or a pharmaceutically acceptable salt or solvate thereof wherein:

$R^1$ is selected from the group consisting of: H, $C_{1-10}$alkyl, Aryl, Heteroaryl and Heterocyclyl, said alkyl, Aryl, Heteroaryl and Heterocyclyl being optionally substituted with one to four substituents independently selected from $R^6$;

$R^2$ is selected from the group consisting of: Aryl, Heteroaryl, Heterocyclyl, $SO_2NR^4R^5$, $NR^4R^5$, $NR^4C(O)R^5$, $NR^4CO_2R^5$, $NR^4SO_2R^5$, $OR^4$ and $C_{1-10}$ alkyl substituted with one to four substituents selected from $R^6$, said Aryl, Heteroaryl and Heterocyclyl being optionally substituted with one to four substituents independently selected from $R^6$, and $R^3$ is selected from the group consisting of: $C_{1-10}$alkyl and Aryl, said alkyl and Aryl being optionally substituted with one to four substituents independently selected from $R^6$;

$R^4$ is selected from the group consisting of: H, $C_{1-10}$alkyl, Aryl, Heteroaryl, Heterocyclyl, said alkyl, Aryl, Heteroaryl, and Heterocyclyl being optionally substituted with one to four substituents independently selected from $R^6$;

$R^5$ is selected from the group consisting of: $C_{1-10}$alkyl, Aryl, Heteroaryl and Heterocyclyl, said alkyl, cycloalkyl, Aryl Heteroaryl, and Heterocyclyl being optionally substituted with one to four substituents independently selected from $R^6$;

or alternatively, $R^4$ and $R^5$ are taken together with the atoms to which they are attached and represent a ring of 5 to 8 members containing 0–2 heteroatoms independently selected from oxygen, sulfur and nitrogen, and optionally substituted with one to four substituents independently selected from $R^6$;

when $R^2$ represents $C_{1-10}$ alkyl, each $R^6$ is independently selected from the group consisting of: halo, Aryl, Heteroaryl, Heterocyclyl, $OR^7$, $SR^7$, $S(O)_mR^8$, $S(O)_2OR^8$, $S(O)_mNR^7R^8$, $NO_2$, $NR^7R^8$, $O(CR^9R^{10})_nNR^7R^8$, $C(O)R^8$, $CO_2R^7$, $CO_2(CR^9R^{10})_nCONR^7R^8$, $OC(O)R^8$, CN, $C(O)NR^7R^8$, $NR^7C(O)R^8$, $OC(O)NR^7R^8$, $NR^7C(O)OR^8$, $NR^7C(O)NR^8R^9$, $CR^7(NOR^8)$, $(CR^9R^{10})_n$-Aryl, $(CR^9R^{10})_n$-Heteroaryl, $(CR^9R^{10})_n$-Heterocyclyl, $CF_3$ and $OCF_3$, and when $R^2$ is other than $C_{1-10}$ alkyl, $R^6$ is independently selected from the group consisting of halo, $C_{1-7}$alkyl, Aryl, Heteroaryl, Heterocyclyl, $OR^7$, $SR^7$, $S(O)_mR^8$, $S(O)_2OR^8$, $S(O)_mNR^7R^8$, $NO_2$, $NR^7R^8$, $O(CR^9R^{10})_nNR^7R^8$, $C(O)R^8$, $CO_2R^7$, $CO_2(CR^9R^{10})_nCONR^7R^8$, $OC(O)R^8$, CN, $C(O)NR^7R^8$, $NR^7C(O)R^8$, $OC(O)NR^7R$, $NR^7C(O)OR^1$, $NR^7C(O)NR^8R^9$, $CR^7(NOR^8)$, $(CR^9R^{10})_n$-Aryl, $(CR^9R^{10})_n$-Heteroaryl, $(CR^9R^{10})_n$-Heterocyclyl, $CF_3$ and $OCF_3$;

wherein m is 0, 1 or 2 and n is an integer from 1 to 7, and the alkyl, Heterocyclyl, Aryl and Heteroaryl groups and portions are optionally substituted with 1–4 substituents selected from a group independently selected from $R^{11}$;

$R^7$, $R^9$ and $R^{10}$ are independently selected from the group consisting of: H, $C_{1-7}$alkyl, Aryl, Ar—$C_{1-10}$alkyl and mono-, di- and tri-halo substituted Ar—$C_{1-10}$alkyl, or one $R^9$ and one $R^{10}$ are taken together with the atoms to which they are attached and any intervening atoms and represent a ring of 3 to 8 members containing 0–2 heteroatoms independently selected from O, S and N;

$R^8$ is selected from the group consisting of: $C_{1-10}$alkyl, Aryl and $C_{1-10}$alkyl-Aryl; and $R^{11}$ is selected from the group consisting of: halo, CN, $C_{1-4}$alkyl, Aryl, $CF_3$ and OH.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, refers to carbon containing groups that are linear, branched or cyclic, and combinations thereof, containing the indicated number of carbon atoms. If no number is specified, 1–10 carbon atoms are intended for linear or branched alkyl groups, and 3–10 carbon atoms are intended for cycloalkyl. When a $C_{1-10}$alkyl group is specified, this includes cycloalkyl groups containing 3–10 atoms. Cycloalkyl is thus a subset of alkyl containing 1–3 carbocyclic rings that are fused. Examples of alkyl groups include methyl, ethyl, propyl, isopropyl, butyl, sec- and tert-butyl, pentyl, hexyl, heptyl, octyl, nonyl and the like "Cycloalkyl" as used herein also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Aryl" (Ar) means mono- and bicyclic aromatic rings containing only carbon atoms. Examples of aryl include phenyl and naphthyl. Ar—$C_{1-10}$alkyl refers to an aryl group attached to an alkyl group at any available point of attachment. Likewise, mon-, di- and tri-halo substituted aralkyl groups have the specified number of halo groups at any available point of attachment.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are nonaromatic or partially aromatic, and aromatic heterocyclic groups fused to cycloalkyl rings.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Preferred heterocyclyl groups include piperidinyl, piperazinyl and pyrrolidinyl.

"Halogen" (Halo) includes fluorine, chlorine, bromine and iodine.

The present invention is directed to a compound represented by formula I:

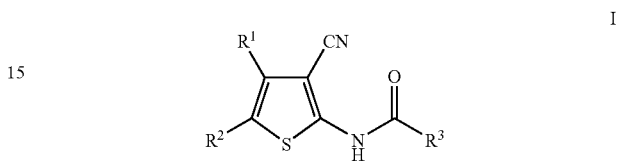

or a pharmaceutically acceptable salt or solvate thereof wherein:

$R^1$ is selected from the group consisting of: H, $C_{1-10}$alkyl, Aryl, Heteroaryl and Heterocyclyl, said alkyl, Aryl, Heteroaryl and Heterocyclyl being optionally substituted with one to four substituents independently selected from $R^6$;

$R^2$ is selected from the group consisting of: Aryl, Heteroaryl, Heterocyclyl, $SO_2NR^4R^5$, $NR^4R^5$, $NR^4C(O)R^5$, $NR^4CO_2R^5$, $NR^4SO_2R^5$, $OR^4$ and $C_{1-10}$ alkyl substituted with one to four substituents selected from $R^6$, said Aryl, Heteroaryl and Heterocyclyl being optionally substituted with one to four substituents independently selected from $R^6$, and $R^3$ is selected from the group consisting of: $C_{1-10}$alkyl and Aryl, said alkyl and Aryl being optionally substituted with one to four substituents independently selected from $R^6$;

$R^4$ is selected from the group consisting of: H, $C_{1-10}$alkyl, Aryl, Heteroaryl, Heterocyclyl, said alkyl, Aryl, Heteroaryl, and Heterocyclyl being optionally substituted with one to four substituents independently selected from $R^6$;

$R^5$ is selected from the group consisting of: $C_{1-10}$alkyl, Aryl, Heteroaryl and Heterocyclyl, said alkyl, cycloalkyl, Aryl Heteroaryl, and Heterocyclyl being optionally substituted with one to four substituents independently selected from $R^6$;

or alternatively, $R^4$ and $R^5$ are taken together with the atoms to which they are attached and represent a ring of 5 to 8 members containing 0–2 heteroatoms independently selected from oxygen, sulfur and nitrogen, and optionally substituted with one to four substituents independently selected from $R^6$;

when $R^2$ represents $C_{1-10}$ alkyl, each $R^6$ is independently selected from the group consisting of: halo, Aryl, Heteroaryl, Heterocyclyl, $OR^7$, $SR^7$, $S(O)_mR^8$, $S(O)_2OR^8$, $S(O)_m NR^7R^8$, $NO_2$, $NR^7R^8$, $O(CR^9R^{10})_nNR^7R^8$, $C(O)R^8$, $CO_2R^7$, $CO_2(CR^9R^{10})_nCONR^7R^8$, $OC(O)R^8$, CN, $C(O)NR^7R^8$, $NR^7C(O)R^8$, $OC(O)NR^7R^8$, $NR^7C(O)OR^8$, $NR^7C(O)NR^8R^9$, $CR^7(NOR^8)$, $(CR^9R^{10})_n$-Aryl, $(CR^9R^{10})_n$-Heteroaryl, $(CR^9R^{10})_n$-Heterocyclyl, $CF_3$ and $OCF_3$, and when $R^2$ is other than $C_{1-10}$ alkyl, $R^6$ is independently selected from the group consisting of halo, $C_{1-7}$alkyl, Aryl, Heteroaryl, Heterocyclyl, $OR^7$, $SR^7$, $S(O)_mR^8$, $S(O)_2OR^8$, $S(O)_mNR^7R^8$, $NO_2$, $NR^7R^8$, $O(CR^9R^{10})_nNR^7R^8$, $C(O)R^8$, $CO_2R^7$, $CO_2(CR^9R^{10})_nCONR^7R^8$, $OC(O)R^8$, CN, $C(O)NR^7R^8$, $NR^7C(O)R^8$, $OC(O)NR^7R^8$, $NR^7C(O)OR^8$, $NR^7C$ (O)NR$^8$R$^9$, CR$^7$(NOR$^8$), (CR$^9$R$^{10}$)$_n$-Aryl, (CR$^9$R$^{10}$)$_n$-Heteroaryl, (CR$^9$R$^{10}$)$_n$-Heterocyclyl, CF$_3$ and OCF$_3$;

wherein m is 0, 1 or 2 and n is an integer from 1 to 7, and the alkyl, Heterocyclyl, Aryl and Heteroaryl groups and portions are optionally substituted with 1–4 substituents selected from a group independently selected from R$^{11}$;

R$^7$, R$^9$ and R$^{10}$ are independently selected from the group consisting of: H, C$_{1-7}$alkyl, Aryl, Ar—C$_{1-10}$alkyl and mono-, di- and tri-halo substituted Ar—C$_{1-10}$alkyl, or one R$^9$ and one R$^{10}$ are taken together with the atoms to which they are attached and any intervening atoms and represent a ring of 3 to 8 members containing 0–2 heteroatoms independently selected from O, S and N;

R$^8$ is selected from the group consisting of: C$_{1-10}$ alkyl, Aryl and C$_{1-10}$alkyl-Aryl; and R$^{11}$ is selected from the group consisting of: halo, CN, C$_{1-4}$alkyl, Aryl, CF$_3$ and OH.

In an aspect of the invention that is of particular interest, a compound of formula I is disclosed wherein R$^1$ represents C$_{1-10}$alkyl, preferably C$_{1-4}$alkyl and more preferably methyl. Within this aspect of the invention, all other variables are as originally defined.

In another aspect of the invention that is of particular interest, a compound of formula I is disclosed wherein R$^2$ is Heteroaryl or Heterocyclyl, each with 0–1 R$^6$ groups attached, NR$^4$R$^5$, or C$_{1-10}$alkyl with 1–2 R$^6$ groups attached. Within this aspect of the invention, all other variables are as originally defined.

In another aspect of the invention that is of particular interest, a compound of formula I is disclosed wherein R$^3$ is C$_{1-10}$alkyl with 0–1 R$^6$ groups attached. Within this aspect of the invention, all other variables are as originally defined.

In another aspect of the invention that is of particular interest, a compound of formula I is disclosed wherein R$^4$ is H or C$_{1-10}$alkyl. Within this aspect of the invention, all other variables are as originally defined.

In another aspect of the invention that is of particular interest, a compound of formula I is disclosed wherein R$^5$ is C$_{1-10}$alkyl having 1–2 R$^6$ groups attached. Within this aspect of the invention, all other variables are as originally defined.

In another aspect of the invention, a compound of formula I is disclosed wherein R$^2$ represents Heteroaryl or Heterocyclyl, each with 1 R$^6$ group attached selected from the group consisting of: C$_{1-4}$alkyl, C$_{3-7}$cycloalkyl, Aryl, Heteroaryl, Heterocyclyl, OR$^7$, (CR$^9$R$^{10}$)$_n$-Aryl, (CR$^9$R$^{10}$)$_n$-Heteroaryl and (CR$^9$R$^{10}$)$_n$-Heterocyclyl. Within this aspect of the invention, all other variables are as originally defined.

In another aspect of the invention, a compound of formula I is disclosed wherein R$^2$ represents NR$^4$R$^5$ wherein R$^4$ is H or C$_{1-10}$alkyl, and R$^5$ is C$_{1-10}$alkyl having 1–2 R$^6$ groups attached. Within this aspect of the invention, all other variables are as originally defined.

In yet another aspect of the invention, a compound of formula I is disclosed wherein R$^2$ represents C$_{1-10}$alkyl with 1–2 R$^6$ groups attached selected from OR$^7$, Aryl, mono-halophenyl and di-halophenyl. Within this aspect of the invention, all other variables are as originally defined.

In yet another aspect of the invention, a compound of formula I is disclosed wherein:

R$^1$ represents C$_{1-10}$alkyl;

R$^2$ represents Heteroaryl or Heterocyclyl with 0–1 R$^6$ groups attached, NR$^4$R$^5$, or C$_{1-10}$alkyl with 1–2 R$^6$ groups attached;

R represents C$_{1-10}$alkyl with 0–1 R$^6$ groups attached;

R$^4$ is H or C$_{1-10}$alkyl;

R$^5$ is C$_{1-10}$alkyl with 1–2 R$^6$ groups attached, and R$^6$ through R$^{11}$ are as originally defined.

In yet another aspect of the invention that is of particular interest, a compound of formula I is disclosed wherein:

R$^1$ represents methyl;

R$^3$ represents 3-pentyl, and R$^2$ is selected from the table below:

| R$^2$ |
|---|

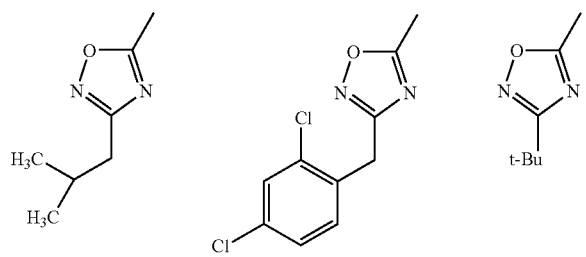

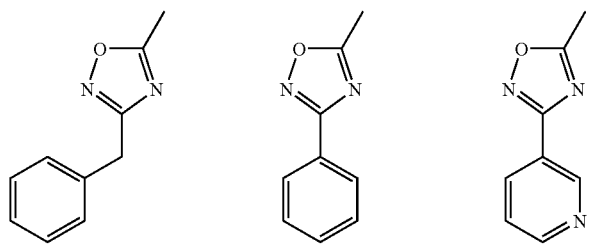

-continued
R²
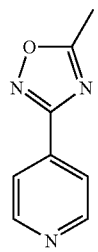 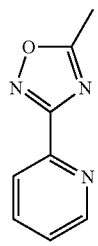 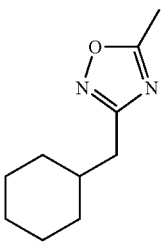
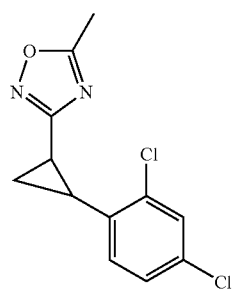 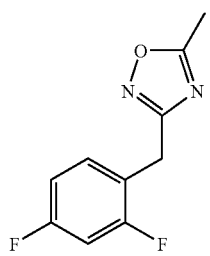 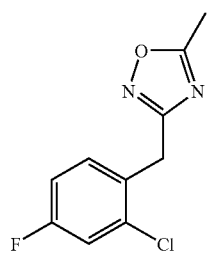
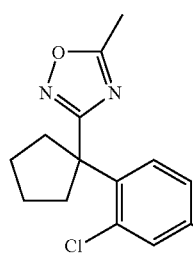 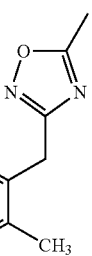 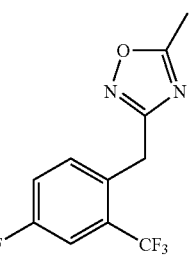
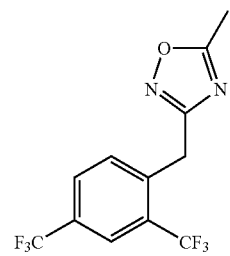 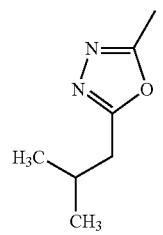 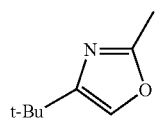
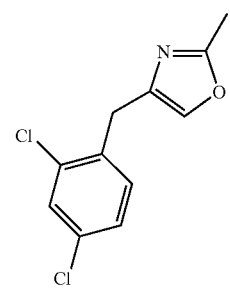 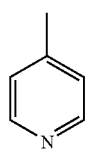 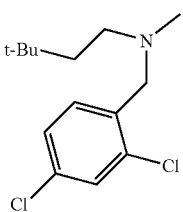

-continued

R²

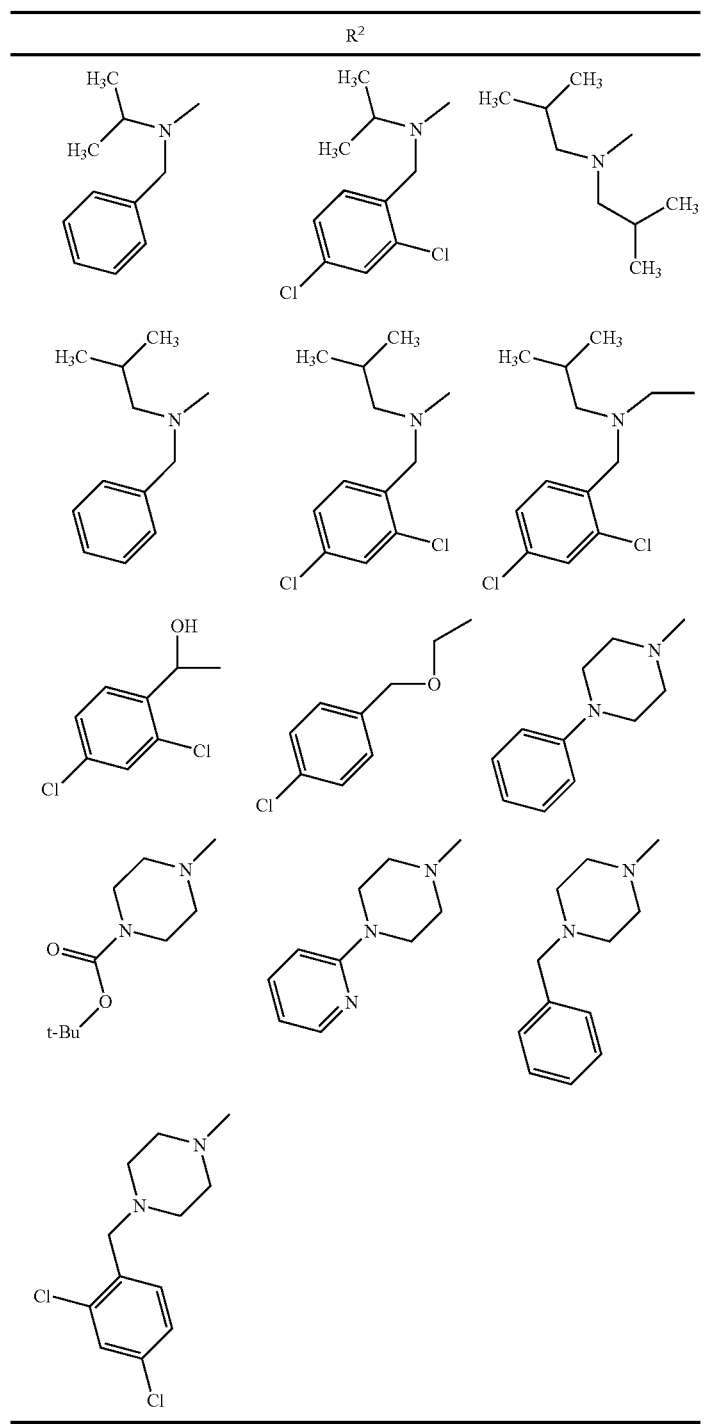

as well as the pharmaceutically acceptable salts and solvates thereof.

Species falling within the scope of the present invention that are of particular interest include the following:

N-[3-cyano-5-(3-isobutyl-1,2,4-oxadiazol-5-yl)-4-methylthien-2-yl]-2-ethylbutanamide;

N-{3-cyano-5-[3-(2,4-dichlorobenzyl)-1,2,4-oxadiazol-5-yl]-4-methylthien-2-yl}-2-ethylbutanamide;

N-[5-(3-tert-butyl-1,2,4-oxadiazol-5-yl)-3-cyano-4-methylthien-2-yl]-2-ethylbutanamide;

N-[5-(3-benzyl-1,2,4-oxadiazol-5-yl)-3-cyano-4-methylthien-2-yl]-2-ethylbutanamide;

N-[3-cyano-4-methyl-5-(3-phenyl-1,2,4-oxadiazol-5-yl)thien-2-yl]-2-ethylbutanamide;

N-[3-cyano-4-methyl-5-(3-pyridin-2-yl-1,2,4-oxadiazol-5-yl)thien-2-yl]-2-ethylbutanamide;

N-[3-cyano-4-methyl-5-(3-pyridin-3-yl-1,2,4-oxadiazol-5-yl)thien-2-yl]-2-ethylbutanamide;
N-[3-cyano-4-methyl-5-(3-pyridin-4-yl-1,2,4-oxadiazol-5-yl)thien-2-yl]-2-ethylbutanamide;
N-{3-cyano-5-[3-(cyclohexylmethyl)-1,2,4-oxadiazol-5-yl]-4-methylthien-2-yl}-2-ethylbutanamide;
N-(3-cyano-5-{3-[1-(2,4-dichlorophenyl)cyclopropyl]-1,2,4-oxadiazol-5-yl}-4-methylthien-2-yl)-2-ethylbutanamide;
N-{3-cyano-5-[3-(2,4-difluorobenzyl)-1,2,4-oxadiazol-5-yl]-4-methylthien-2-yl}-2-ethylbutanamide;
N-{5-[3-(2-chloro-4-fluorobenzyl)-1,2,4-oxadiazol-5-yl]-3-cyano-4-methylthien-2-yl}-2-ethylbutanamide;
N-(5-{3-[1-(2-chloro-4-fluorophenyl)cyclopentyl]-1,2,4-oxadiazol-5-yl}-3-cyano-4-methylthien-2-yl)-2-ethylbutanamide;
N-{3-cyano-5-[3-(mesitylmethyl)-1,2,4-oxadiazol-5-yl]-4-methylthien-2-yl}-2-ethylbutanamide;
N-(3-cyano-5-{3-[4-fluoro-2-(trifluoromethyl)benzyl]-1,2,4-oxadiazol-5-yl}-4-methylthien-2-yl)-2-ethylbutanamide;
N-(5-{3-[2,4-bis(trifluoromethyl)benzyl]-1,2,4-oxadiazol-5-yl}-3-cyano-4-methylthien-2-yl)-2-ethylbutanamide;
N-[3-cyano-5-(5-isobutyl-1,3,4-oxadiazol-2-yl)-4-methylthien-2-yl]-2-ethylbutanamide;
N-[5-(4-tert-butyl-1,3-oxazol-2-yl)-3-cyano-4-methylthien-2-yl]-2-ethylbutanamide;
N-{3-cyano-5-[4-(2,4-dichlorobenzyl)-1,3-oxazol-2-yl]-4-methylthien-2-yl}-2-ethylbutanamide;
N-(3-cyano-4-methyl-5-pyridin-4-ylthien-2-yl)-2-ethylbutanamide;
N-{3-cyano-5-[(2,4-dichlorobenzyl)(3,3-dimethylbutyl)amino]-4-methylthien-2-yl}-2-ethylbutanamide;
N-{5-[benzyl(isopropyl)amino]-3-cyano-4-methylthien-2-yl}-2-ethylbutanamide;
N-{3-cyano-5-[(2,4-dichlorobenzyl)(isopropyl)amino]-4-methylthien-2-yl}-2-ethylbutanamide;
N-[3-cyano-5-(diisobutylamino)-4-methylthien-2-yl]-2-ethylbutanamide;
N-{5-[benzyl(isobutyl)amino]-3-cyano-4-methylthien-2-yl}-2-ethylbutanamide;
N-{3-cyano-5-[(2,4-dichlorobenzyl)(isobutyl)amino]-4-methylthien-2-yl}-2-ethylbutanamide;
N-{3-cyano-5-[(2,4-dichlorophenyl)(hydroxy)methyl]-4-methylthien-2-yl}-2-ethylbutanamide;
N-(3-cyano-5-{[(2,4-dichlorobenzyl)(isobutyl)amino]methyl}-4-methylthien-2-yl)-2-ethylbutanamide;
N-[3-cyano-4-methyl-5-(4-phenylpiperazin-1-yl)thien-2-yl]-2-ethylbutanamide;
tert-butyl 4-{4-cyano-5-[(2-ethylbutanoyl)amino]-3-methylthien-2-yl}piperazine-1-carboxylate;
N-[3-cyano-4-methyl-5-(4-pyridin-2-ylpiperazin-1-yl)thien-2-yl]-2-ethylbutanamide;
N-[5-(4-benzylpiperazin-1-yl)-3-cyano-4-methylthien-2-yl]-2-ethylbutanamide;
N-{3-cyano-5-[4-(2,4-dichlorobenzyl)piperazin-1-yl]-4-methylthien-2-yl}-2-ethylbutanamide; and
N-(5-{[(4-chlorobenzyl)oxy]methyl}-3-cyano-4-methylthien-2-yl)-2-ethylbutanamide, as well as the pharmaceutically acceptable salts and solvates of the compounds listed above.

The invention further includes a pharmaceutical composition which is comprised of a compound of formula I or a pharmaceutically acceptable salt or solvate thereof in combination with a pharmaceutically acceptable carrier.

Also included is a method of treating type 2 diabetes mellitus in a mammalian patient in need of such treatment, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included in a method of treating, preventing or delaying the onset of diseases or conditions that are associated with type 2 diabetes mellitus. Examples include diseases and conditions selected from the group consisting of: dyslipidemias, such as elevated levels of cholesterol, triglycerides or low density lipoproteins (LDL), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, ptoluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of formula I herein include the pharmaceutically acceptable salts and solvates.

This invention relates to a method of antagonizing or inhibiting the production or activity of glucagon, thereby reducing the rate of gluconeogenesis and glycogenolysis, and the concentration of glucose in plasma. In this aspect of the invention, the compound is administered to a mammalian patient in need of such treatment in an amount effective to antagonize or inhibit the production or activity of glucagon.

The compounds of formula I can be used in the manufacture of a medicament for the prophylactic or therapeutic treatment of disease states in mammals in which elevated levels of glucose are found. The process entails combining a compound of formula I or a pharmaceutically acceptable salt or solvate thereof with the carrier.

Dose Ranges

The prophylactic or therapeutic dose of a compound of Formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases.

When intravenous or or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of Formula I:

| Injectable Suspension (I.M.) | mg/mL | Tablet | mg/tablet |
|---|---|---|---|
| Compound of Formula I | 10 | Compound of Formula I | 25 |
| Methylcellulose | 5.0 | Microcrystalline Cellulose | 415 |
| Tween 80 | 0.5 | Povidone | 14.0 |

| -continued | | | |
|---|---|---|---|
| Benzyl alcohol | 9.0 | Pregelatinized Starch | 43.5 |
| Benzalkonium chloride | 1.0 | Magnesium Stearate | 2.5 |
| Water for injection to make | 1.0 mL | Total | 500 mg |
| Capsule | mg/capsule | Aerosol | Per canister |
| Compound of Formula I | 25 | Compound of Formula I | 24 mg |
| Lactose Powder | 573.5 | Lecithin, NF Liq. Conc. | 1.2 mg |
| Magnesium Stearate | 1.5 | Trichlorofluoromethane, NF | 4.025 g |
| Total | 600 mg | Dichlorodifluoromethane, NF | 12.15 g |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) bis-guanides (e.g., buformin, metformin, phenformin), (b) PPAR agonists (e.g., troglitazone, pioglitazone, rosiglitazone), (c) insulin, (d) somatostatin, (e) α-glucosidase inhibitors (e.g., voglibose, miglitol, acarbose), and (f) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Throughout the instant application, the following abbreviations are used with the following meanings unless otherwise indicated:

| | |
|---|---|
| Bu = butyl | Bn = benzyl |
| BOC, Boc = t-butyloxycarbonyl | CBZ, Cbz = Benzyloxycarbonyl |
| DCC = Dicyclohexylcarbodiimide | DCM = dichloromethane |
| DIPEA = diisopropylethylamine | DMF = N,N-dimethylformamide |
| DMAP = 4-Dimethylaminopyridine | Et = ethyl |
| EtOAc = ethyl acetate | EtOH = ethanol |

| -continued | |
|---|---|
| eq. = equivalent(s) | FAB-mass spectrum = Fast atom bombardment-mass spectroscopy |
| HOAc = acetic acid | HPLC = High pressure liquid chromatography |
| HOBT, HOBt = Hydroxybenztriazole | LAH = Lithium aluminum hydride |
| Me = methyl | PBS = phosphate buffer saline |
| Ph = phenyl | TFA = Trifluoroacetic acid |
| THF = Tetrahydrofuran | TMS = Trimethylsilane |

Compounds of the present invention may be prepared according to the methodology outlined in the following Schemes. In Scheme 1, a ketone 1 is condensed with malononitrile 2 in the presence of sulfur ($S_8$) and a dialkylamine (such as morpholine) in ethanol according to methods described in the literature (S. Mukherjee and A. De, J. Chem. Res. 8, 295 (1994); M. S. Mahas et al. J. Chem. Soc. 1969, (1937); A. De et al. J. Het. Chem. 29, 1213 (1992)) to afford the 2-amino-3-cyano-thiophene 3. Acylation of 3 with an appropriate anhydride or acid chloride in the presence of a trialkylamine (e.g., triethylamine or N-methylmorpholine) according to published procedures (U. Sensfuss et al. Heteroat. Chem. 9, 529 (1998)) will afford the amide 4 corresponding to the general formula I.

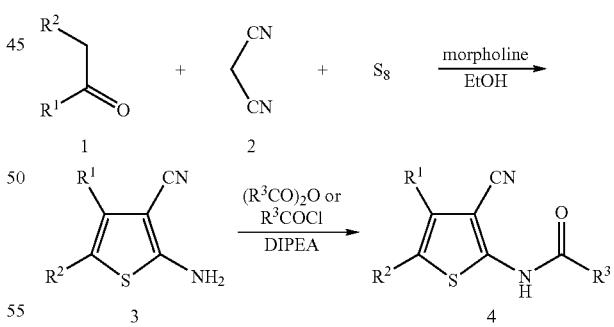

Scheme 1.

In some instances it may be necessary to carry out the thiophene synthesis in two steps, as illustrated in Scheme 2. A dicyano-alkene 5 is prepared by condensation of a ketone such as 1 and malononitrile. This intermediate is reacted with sulfur ($S_8$) and a dialkylamine (e.g., morpholine) in ethanol according to methods described in the literature (A. Rajca and M. Tisler, Monatch. Chem. 121, 697 (1990); B. Naumann et al., Pharmazie 53, 4 (1996)) to afford 2-amino-3-cyano-thiophene 3. Acylation of 3 with an appropriate anhydride or acid chloride in the presence of a trialkylamine (e.g., diisopropylethylamine) according to published procedures (U. Sensfuss et al. Heteroat. Chem. 9, 529 (1998)) will afford the thiopheneamide represented by formula I.

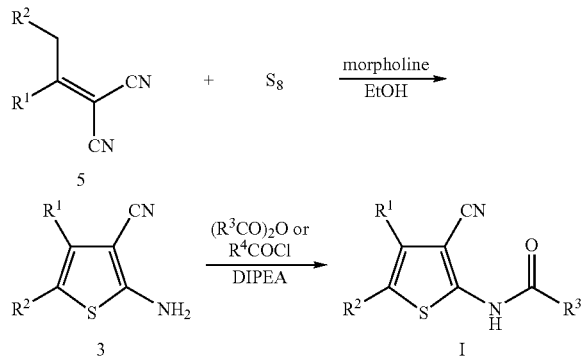

It is recognized that when the ketone 1 is not a symmetrically substituted ketone, the product 3 may be formed as a mixture of positional isomers. These isomers may be separated at any stage in the synthetic sequence by preparative thin layer chromatography, flash chromatography on silica gel as described by W. C. Still et al., *J. Org. Chem.*, 43, 2923 (1978), or HPLC. Compounds that are purified by HPLC may be isolated as the corresponding salt.

A wide variety of ketones corresponding to 1 are commercially available, known in the literature, or may be conveniently prepared by a variety of methods known to those skilled in the art. One such example of a ketone that may be used in the synthesis of compounds of the general formula I is tert-butyl 3-oxoalkanoate 6 in Scheme 3. The intermediate 7 is obtained as illustrated in Scheme 1, followed by acylation to afford intermediate 8.

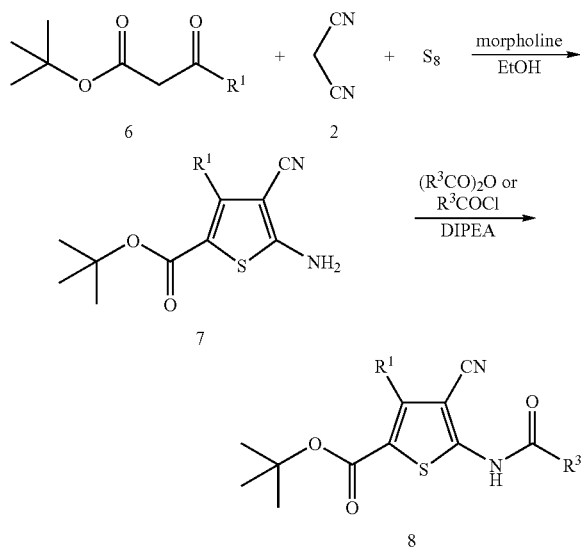

Intermediate 8 from Scheme 3 may be further manipulated to derive other compounds of the present invention. As illustrated in Scheme 4, the tert-butyl ester may be removed to reveal the carboxylate 9 using acidic conditions such as trifluoromethylacetic acid in an aprotic solvent such as dichloromethane at 0–50° C. for 3–48 h. The carboxylate intermediate 9 may be esterified to form compounds such as 10 by a variety of methods. Two such methods are also illustrated in Scheme 4. In the first such method, the free acid may be combined with an alkyl bromide in the presence of a tertiary amine base such as di-iso-propylethylamine in an organic solvent such as dichloromethane at 20–50° C. for 3–48 h, to afford the corresponding ester 10. Alternatively, the carboxylate intermediate 9 may be activated with a coupling reagent such as 2-chloro-1-methylpyridinium iodide in the presence of a tertiary amine base such as di-iso-propylethylamine in an organic solvent such as dichloromethane at 20–50° C. for 3–48 h, to afford the corresponding ester 10.

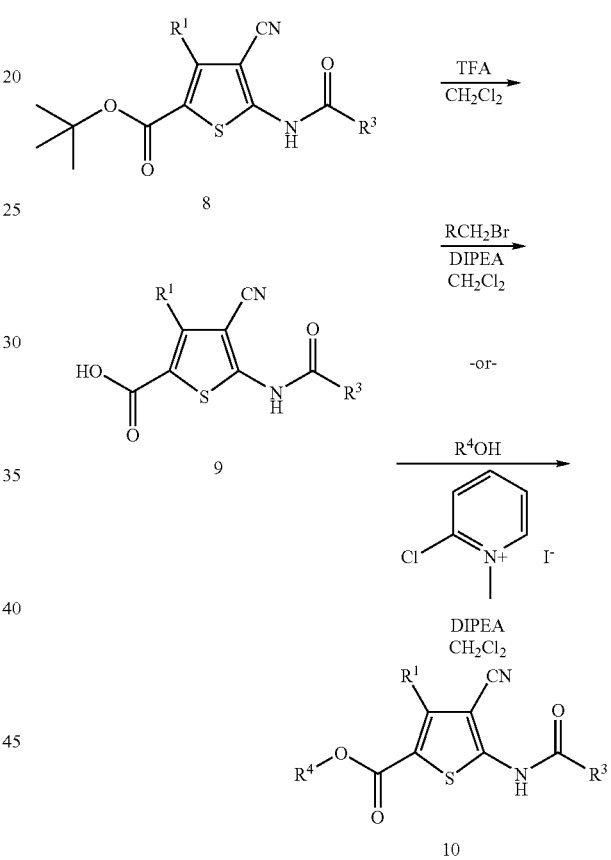

The carboxylic acid moiety from intermediate 9 may be converted to form a heterocyclic ring to afford additional derivatives that correspond to formula 1. One such method reported in the literature involves the formation of a 1,2,4-oxadiazole by condensation with an amidoxime (Liang, G. B.; Feng, D. D. *Tet. Lett.* 37, 6627–6630 (1996)), as illustrated in Scheme 5. The amidoxime 12 may be readily prepared from the corresponding nitrile 11, which is also illustrated in Scheme 5. A variety of nitriles are commercially available, known in the literature, or may be readily prepared by those skilled in the art. The nitrile may be combined with hydroxylamine hydrochloride in the presence of an inorganic base such as sodium carbonate in a 6:1 mixture of water and ethyl alcohol at 100° C. for 3–48 h to form the corresponding amidoxime derivative 12. This material may then be combined with the acid intermediate 9 in the presence of at least two equivalents of an amide coupling reagent such as benztriazole-1-yl-oxy-tris-pyrrolidino-phosphonium hexafluorophosphate (PyBop) in dimethylformamide (DMF) at 95° C. for 3–48 h to form the corresponding 1,2,4-oxadiazole derivative 13.

Scheme 5.

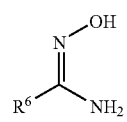

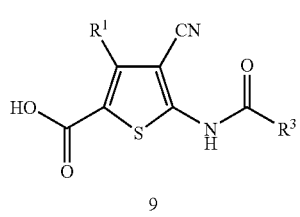

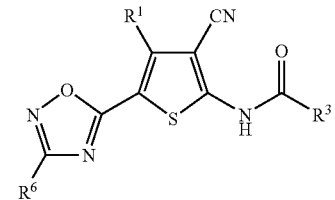

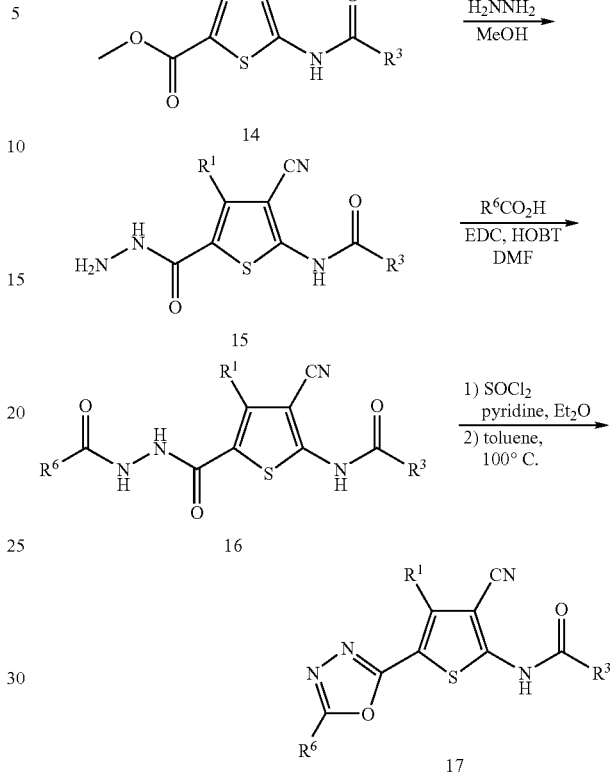

The analogous 1,3,4-oxadiazole derivatives corresponding to formula I may also be synthesized from the acid intermediate 9, as illustrated in Scheme 6, using procedures known from the literature (Borg, S.; Estenne-Bouhtou, G.; Luthman, K.; Csoregh, I.; Hesselink, W.; Hacksell, U. *J. Org. Chem.* 60, 3122–3120 (1995). Thus the acid 9 may be converted to the corresponding methyl ester 14 using methanol and a coupling reagent such as 1-ethyl-3-(3'-dimethylaminopropyl)carbodiimide (EDC). This material may then be converted to the hydrazide 15 by heating the ester with hydrazine in methanol at 65° C. for 3–48 h. Acylation of the hydrazide may be accomplished with a variety of carboxylic acids $R^6CO_2H$ under standard coupling conditions outlined above to afford the acylhydrazide intermediate 16. Cyclization of this intermediate to form the 1,3,4-oxadiazole derivative may be accomplished in two steps. First, the acylhydrazide is treated with thionyl chloride in the presence of a mild base such as pyridine in ether at 0° C., followed by heating to 100° C. in toluene, to afford the 1,3,4-oxadiazole derivative 17.

Scheme 6.

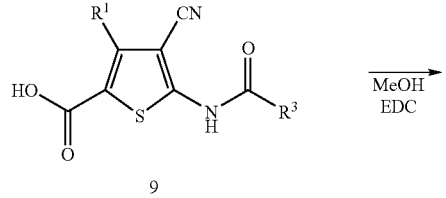

An additional example of a heteroaryl derivative of intermediate 9 that corresponds to formula I is illustrated by the formation of the oxazole derivative in Scheme 7. The amide derivative of 9 may first be prepared in two steps by coupling of the acid to N-hydroxysuccinimide using 1-ethyl-3-(3'-dimethylaminopropyl)carbodiimide (EDC) in dichloromethane at ambient temperature to afford the succinate ester 18. This intermediate may then be condensed with ammonium hydroxide in an organic solvent such as dioxane at ambient temperature for 3–48 h to afford the primary amide derivative 19. The oxazole derivative is then formed by condensation of the primary amide 19 with an α-bromoketone 20. A variety of α-bromoketones are commercially available, known in the literature, or may be readily prepared by those skilled in the art. This condensation at elevated temperature (80° C. for 3–48 h) affords the oxazole derivative 21 directly.

Scheme 7.

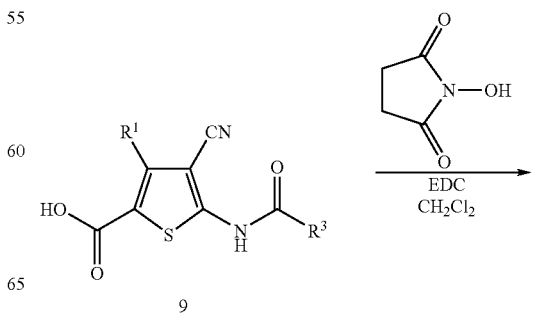

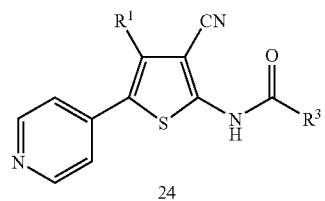

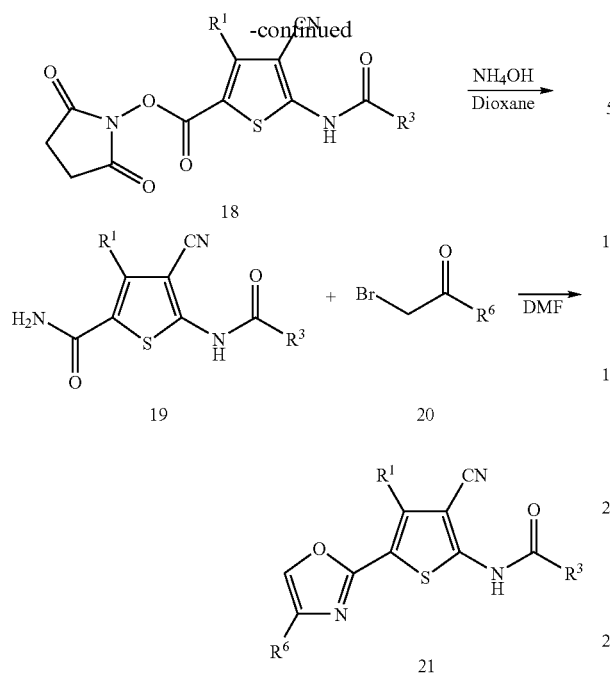

Other examples of heteroaryl derivatives of intermediate 9 that correspond to formula I arise from the organometallic coupling chemistry of the brominated derivative. The 2-bromothiophene analog of intermediate 9 may be readily generated as illustrated in Scheme 8, using a procedure reported in the literature (Zwanenburg, D. J.; Wynberg, H. *Recl. Trav. Chim. Pays-Bas.* 88, 321 (1969)). Thus the slow addition of bromine to the acid intermediate 9 in the presence of aqueous sodium hydroxide at ambient temperature affords the corresponding bromothiophene intermediate 22. This intermediate may be coupled with aryl or heteroaryl boronic acids, which are commercially available, are reported in the literature, or may be readily prepared by those skilled in the art. Organometallic coupling may be accomplished using a palladium catalyst such as tris(dibenzylidineacetone)dipalladium in the presence of an inorganic base such as sodium carbonate in an organic solvent such as 1,2-dimethoxyethane (DME), to afford the coupled derivative 24.

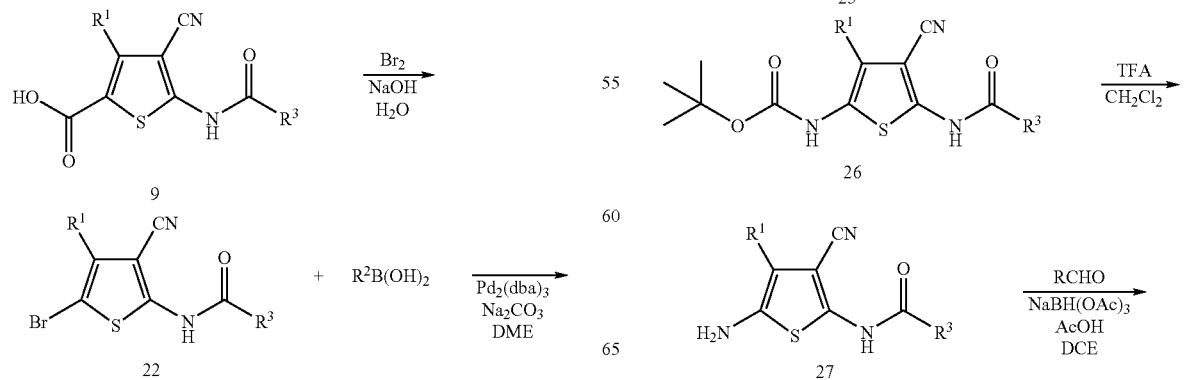

The carboxylic acid intermediate 9 may alternatively be converted to the corresponding amino derivatives, as illustrated in Scheme 9. Treatment of the acid with diphenylphosphoryl azide (DPPA) in the presence of a tertiary amine base such as triethylamine in toluene at ambient temperature for 3–48 h affords the acylazide intermediate 25. This material may then be treated with tert-butanol at 110° C. for 24 h in the presence of triethylamine to afford the N-Boc protected 2-aminothiophene 26. The Boc group may be removed under acidic conditions, to give the free amino derivative 27. Combination of this intermediate with an aldehyde in the presence of a reducing agent such as sodium triacetoxyborohydride, in the presence of a mild acid such as acetic acid, in dichloroethane at ambient temperature for 3–48 h affords the mono-substituted aminothiophene intermediate 28. This final procedure may be repeated with the same or a different aldehyde reagent to afford the bis-substituted aminothiophene derivative 29.

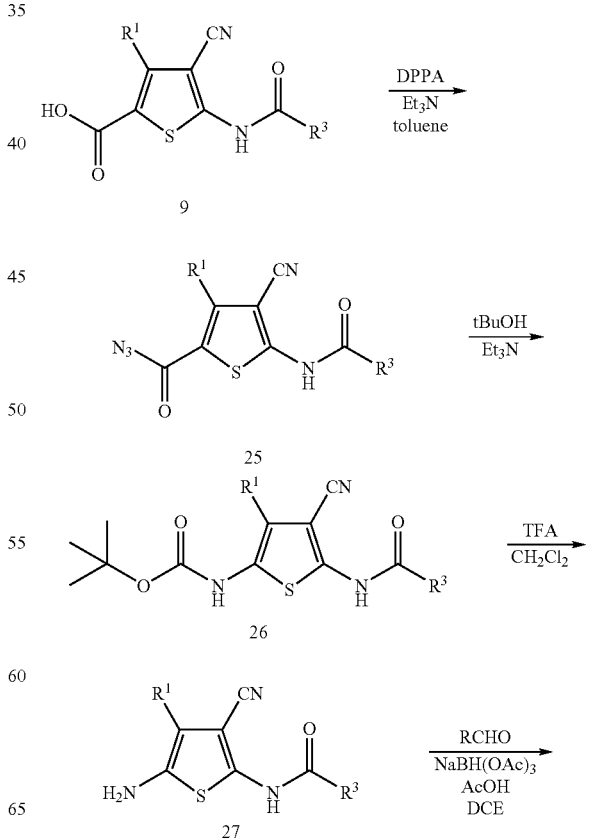

-continued

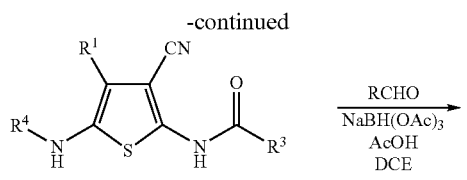

28

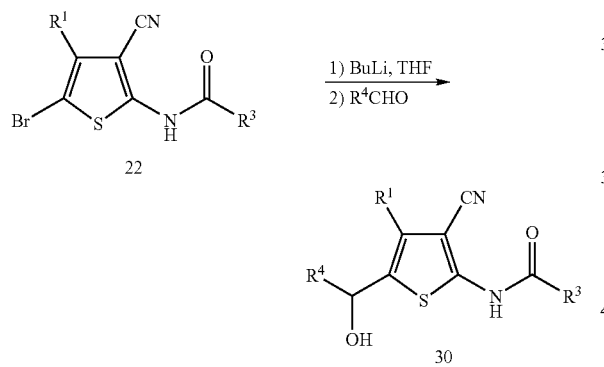

The bromothiophene intermediate 22 from Scheme 8 may be elaborated in a variety of alternative ways to afford compounds that correspond to the general formula I. For example, the intermediate may be treated with butyllithium in tetrahydrofuran at a temperature that does not exceed −78° C., followed by the addition of an aldehyde, which affords the secondary alcohol derivative 30.

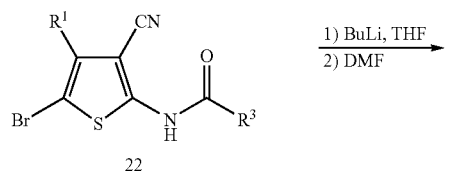

In another example, the bromothiophene intermediate 22 may be treated with butyllithium as in Scheme 10, followed by the addition of dimethylformamide, which affords the corresponding aldehyde 31 as illustrated Scheme 11. This aldehyde may then be combined with a primary amine in the presence of a reducing agent such as sodium triacetoxyborohydride in the presence of a mild acid such as acetic acid in an organic solvent such as 1,2-dichloroethane (DCE) to afford the methylenaminothiophene derivative 32. This intermediate may be further elaborated by the addition of an aldehyde under the above reducing conditions to afford the bis-substituted methyleneaminothiophene derivative 33.

-continued

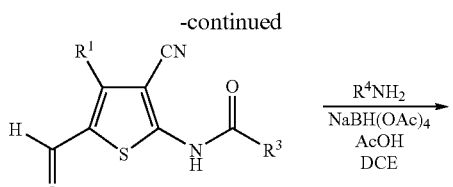

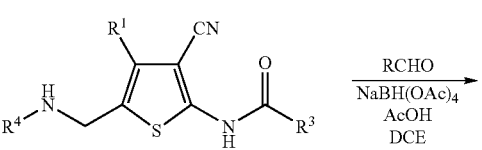

An alternative method that is used in the present invention to prepare aminothiophenes that correspond to the general formula I is illustrated in Scheme 12, and this route has been reported in the literature (Pinto, I. L.; Jarvest, R. L.; Serafinowska, H. T. *Tet. Lett.* 41, 1597–1600 (2000)). In this example an α-phenoxyketone such as 34 may be combined with cyanoacetic acid ethyl ester, a mono-protected piperazine such as N-boc-piperazine, and elemental sulfur in ethanol at 100° C. for 24 h to afford the bis-aminothiophene ester intermediate 37. This intermediate may be acylated with either an acid chloride or acid anhydride in the presence of a tertiary amine base such as di-iso-propylethylamine to afford the acylated intermediate 38. The ester moiety may then be hydrolyzed with aqueous lithium hydroxide in THF at ambient temperature for 24 h to afford the free carboxylic acid intermediate 39. Coupling of this intermediate with N-hydroxysuccinimide using 1-ethyl-3-(3'-dimethylaminopropyl)carbodiimide (EDC) in dichloromethane at ambient temperature affords the succinate ester 40. This substituent may then be converted to the corresponding nitrile in two steps by treating the succinate ester first with 30% ammonium hydroxide in dioxane at ambient temperature for 3 h, followed by dehydration of the resulting primary amide with cyanuric chloride in DMF at ambient temperature, which affords the nitrile derivative 41. This derivative may be further manipulated by cleavage of the carbamate protecting group with trifluoroacetic acid in dichloromethane at ambient temperature for 1 h to afford the free secondary amine. This material may then be combined with an aldehyde and a reducing agent such as sodium triacetoxyborohydride, in the presence of a mild acid such as acetic acid in 1,2-dichloroethane, to afford the piperazenylthiophene derivative 46.

Scheme 12.

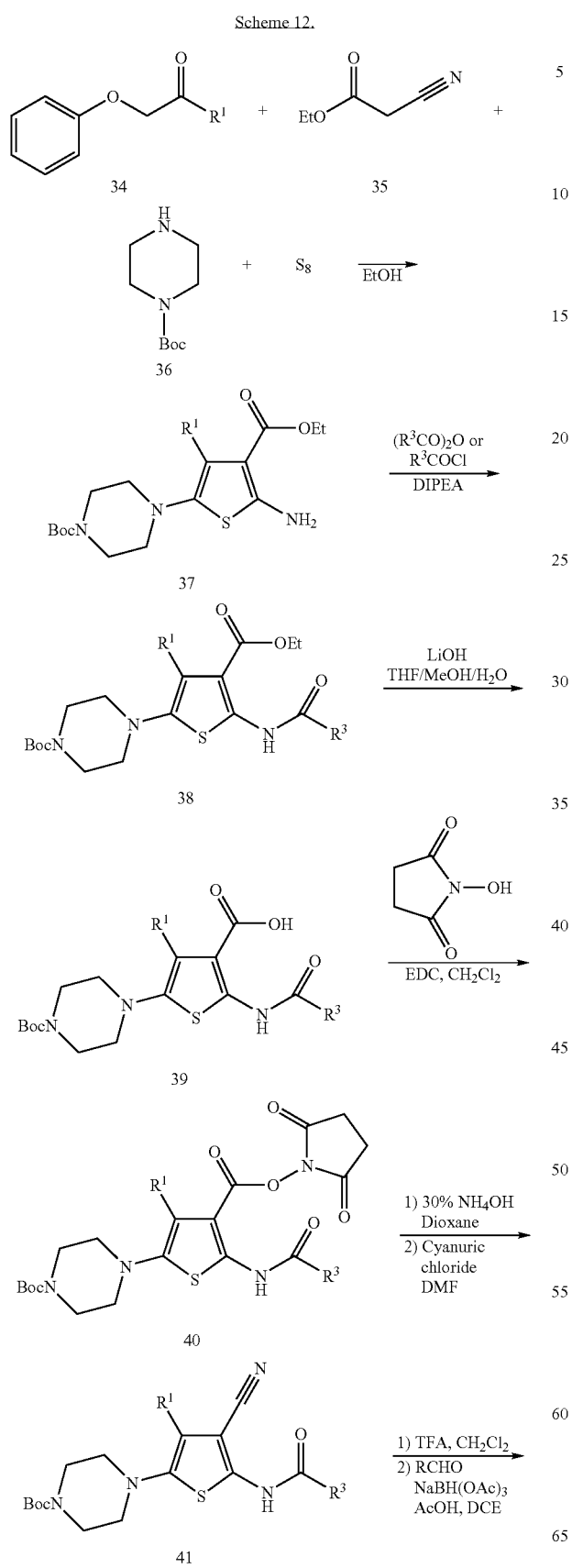

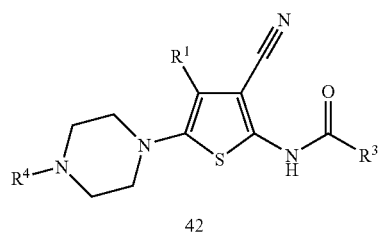

42

The following examples are provided so that the invention might be more fully understood. These examples are illustrative only and should not be construed as limiting the invention in any way.

PREPARATIVE EXAMPLE 1

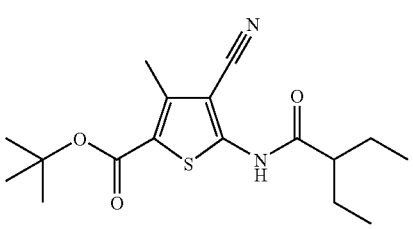

Step A. tert-Butyl 5-amino-4-cyano-3-methylthiophene-2-carboxylate. The title compound was prepared via the sequence outlined in Scheme 1. Thus to 3.32 mL (20.0 mmol) of tert-butyl 3-oxobutanoate in 50 mL of EtOH was added 1.30 mL (20.0 mmol) of malononitrile, followed by 2.62 mL (30.0 mmol) of morpholine, then 0.640 g (20.0 mmol) of elemental sulfur. The mixture was heated to 70° C. for 2 h, then cooled to ambient temperature and purified directly by flash chromatography (30% EtOAc in hexanes), affording the title compound as a beige solid. $^1$H NMR (500 MHz, CDCl$_3$) 5.25 (s, 2H), 2.51 (s, 3H), 1.57 (s, 9H); mass spectrum (ES) m/e=183 (M+H minus tert-butyl).

Step B. tert-Butyl 4-cyano-5-[(2-ethylbutanoyl)amino]-3-methylthiophene-2-carboxylate. To 2.38 g (10.0 mmol) of the intermediate prepared in Step A in 30 mL of dichloromethane was added 1.74 mL (10.0 mmol) of di-isopropylethylamine, followed by 1.38 mL (10.0 mmol) of 2-ethylbutanoyl chloride. After 4 h at ambient temperature, the mixture was diluted with an equal volume of saturated aqueous NaHCO$_3$ and extracted twice with dichloromethane. The combined organic layers were dried (Na$_2$SO$_4$) and concentrated in vacuo. Purification of 100 mg of the extract by reverse phase preparative HPLC afforded the title compound as a white solid. $^1$H NMR (500 MHz, CDCl$_3$) 8.61 (s, 1H), 5.02 (s, 3H), 2.33 (m, 1H), 1.78 (m, 2H), 1.69 (m, 2H), 1.57 (s, 9H), 0.95 (t, J=7.5 Hz, 6H); mass spectrum (ES) m/e=337.2 (M+H).

PREPARATIVE EXAMPLE 2

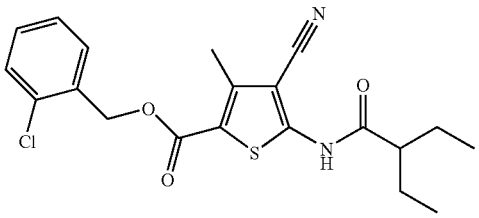

Step A. 4-Cyano-5-[(2-ethylbutanoyl)amino]-3-methylthiophene-2-carboxylic acid. The title compound from Preparative Example 1 was dissolved in 10 mL of CH$_2$Cl$_2$, and to this solution was added 10 mL of trifluoroacetic acid. After 1 h at ambient temperature, the reaction was concentrated in vacuo, and passed through a short plug of silica, eluting with 30% EtOAc in hexane. This afforded the title compound as a white solid. $^1$H NMR (500 MHz, CD$_3$OD) 2.63 (m, 1H), 2.58 (s, 3H), 1.69 (m, 2H), 1.60 (m, 2H), 0.94 (t, J=7.3 Hz, 6H); mass spectrum (ES) m/e=281.2 (M+H).

Step B. 2-Chlorobenzyl 4-cyano-5-[(2-ethylbutanoyl)amino]-3-methylthiophene-2-carboxylate. To a solution of 0.070 g (0.250 mmol) of the intermediate prepared in step A in 2 mL of CH$_2$Cl$_2$ was added 0.087 mL of di-iso-propylethylamine, followed by 0.032 mL (0.250 mmol) of 2-chlorobenzylbromide. After 24 h at ambient temperature, the reaction was diluted with 20 mL of CH$_2$Cl$_2$, followed by washing with 20 mL of 1 N aqueous NaOH, then 1 N aqueous HCl. The organic layer was dried (Na$_2$SO$_4$) and concentrated in vacuo. The crude material was purified by preparative reversed phase HPLC, affording the title compound as a white solid. $^1$H NMR (500 MHz, CDCl$_3$) 8.86 (s, 1H), 7.49 (m, 1H), 7.43 (m, 1H), 7.30 (m, 2H), 5.42 (s, 2H), 2.65 (s, 3H), 2.34 (m, 1H), 1.74 (m, 2H), 1.64 (m, 2H), 0.98 (t, J=7.5 Hz, 6H); mass spectrum (ES) m/e=405.2 (M+1).

EXAMPLE 1

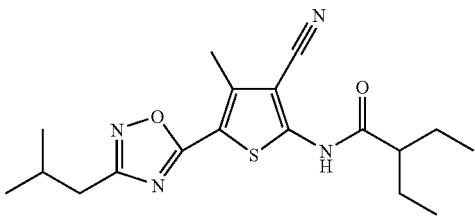

Step A. (1Z)-N'-Hydroxy-3-methylbutanimidamide. To a solution of 2.08 g (25.0 mmol) of 3$$-methylbutanenitrile in 50 mL of ethanol was added 3.82 g (55.0 mmol) of hydroxylamine hydrochloride, followed by 8.01 mL (57.5 mmol) of triethylamine. The reaction was heated to reflux for 16 h, then cooled to ambient temperature and filtered. The solution was concentrated in vacuo. The residue was suspended in diethyl ether and the remaining triethylammonium hydrochloride was filtered. The solution was filtered, and the crude product was used without further purification.

$^1$H NMR (500 MHz, CDCl$_3$) 4.60 (s, 1H), 1.95 (d, 2H), 1.85 (sept., 1H), 0.90 (d, 6H); mass spectrum (ES) m/e=117.1 (M+H).

Step B. N-[3-Cyano-5-(3-isobutyl-1,2,4-oxadiazol-5-yl)-4-methylthien-2-yl]-2-ethylbutanamide. To a solution of 0.100 g (0.350 mmol) of the intermediate prepared in Preparative Example 2 Step A, in 3 mL of DMF was added 0.058 g (0.350 mmol) of CDI. After stirring for 1 h at ambient temperature, to the solution was added 0.041 g (0.350 mmol) of the intermediate prepared in Example 1, Step A. After 16 h at ambient temperature the reaction was diluted with 100 mL of EtOAc and washed with saturated aqueous NaHCO$_3$, and brine. The organic layer was dried (MgSO$_4$) and concentrated in vacuo. Purification by preparative thin layer chromatography (10% EtOAc in hexane) afforded the title compound as a white solid. $^1$H NMR (500 MHz, CDCl$_3$) 8.85 (s, 1H), 2.67 (s, 2H), 2.62 (d, J=7.0 Hz, 2H), 2.32 (m, 1H), 2.16 (sept., J=7.0 Hz, 1H), 1.74 (m, 2H), 1.64 (m, 2H), 0.98 (d, J=7.0 Hz, 6H), 0.94 (t, J=7.5 Hz, 6H); mass spectrum (ES) m/e=361.3 (M+H).

EXAMPLE 2

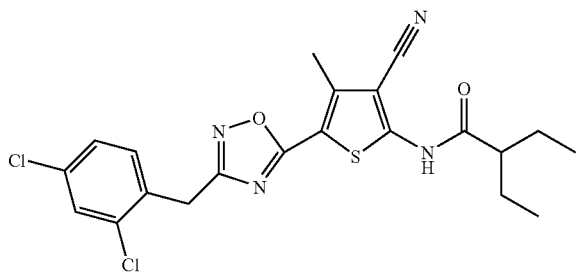

Step A. (1Z)-2-(2,4-Dichlorophenyl)-N'-hydroxyethanimidamide. The intermediate was prepared from 4.65 g (25.0 mmol) of (2,4-dichlorophenyl)acetonitrile using the procedure from Example 1, step A, affording the title compound as a white solid. Mass spectrum (ES) m/e=219.0 (M+H).

Step B. N-{3-Cyano-5-[3-(2,4-dichlorobenzyl)-1,2,4-oxadiazol-5-yl]-4-methylthien-2-yl}-2-ethylbutanamide.
The title compound was prepared from 0.500 g (1.78 mmol) of the intermediate prepared in Preparative Example 2, step A, and 0.390 g (1.78 mmol) of the intermediate prepared in Example 2, step A, using the procedure from Example 1, step B. Purification of the crude material by flash chromatography (20% EtOAc in hexane) afforded the title compound as a white solid. $^1$H NMR (500 MHz, CDCl$_3$) 8.96 (s, 1H), 7.40 (d, J=2.0 Hz, 1H), 7.29 (d, J=8.5 Hz, 1H), 7.21 (dd, J=2.0 Hz, J=8.5 Hz, 1H), 4.19 (s, 2H), 2.64 (s, 3H), 2.33 (m, 1H), 1.73 (m, 2H), 1.63 (m, 2H), 0.93 (t, J=7.5 Hz, 6H); mass spectrum (ES) m/e=525.2 (M+H).

The compounds in the following examples were prepared from the intermediate prepared in Preparative Example 2, step A, and the corresponding imidamides using the procedure from Example 2, step B.

EXAMPLE 3

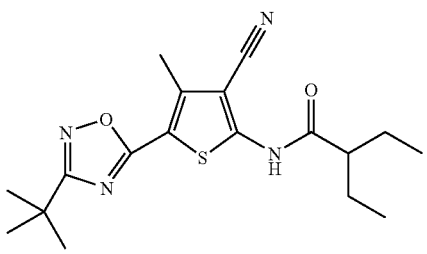

N-[5-(3-tert-Butyl-1,2,4-oxadiazol-5-yl)-3-cyano-4-methylthien-2-yl]-2-ethylbutanamide. $^1$H NMR (500 MHz, CDCl$_3$) 9.73 (s, 1H), 2.64 (s, 3H), 2.44 (m, 1H), 1.74 (m, 2H), 1.62 (m, 2H), 1.36 (s, 9H), 0.93 (t, J=7.5 Hz, 6H); mass spectrum (ES) m/e=361.2 (M+H).

EXAMPLE 4

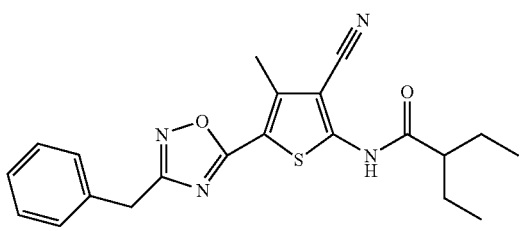

N-[5-(3-Benzyl-1,2,4-oxadiazol-5-yl)-3-cyano-4-methylthien-2-yl]-2-ethylbutanamide. $^1$H NMR (500 MHz, CDCl$_3$) 9.45 (s, 1H), 7.36 (d, J=7.5 Hz, 2H), 7.31 (t, J=8.0 Hz, 2H), 7.24 (t, J=7.5 Hz, 1H), 4.08 (s, 2H), 2.64 (s, 3H), 2.38 (m, 1H), 1.73 (m, 2H), 1.63 (m, 2H), 0.94 (t, J=7.5 Hz, 6H); mass spectrum (ES) m/e=395.2 (M+H).

EXAMPLE 5

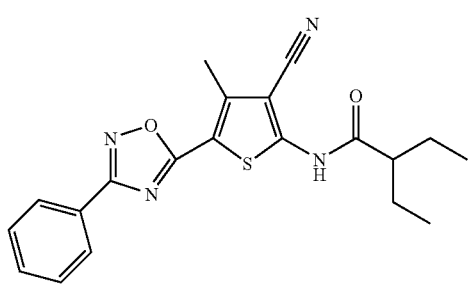

N-[3-Cyano-4-methyl-5-(3-phenyl-1,2,4-oxadiazol-5-yl)thien-2-yl]-2-ethylbutanamide. $^1$H NMR (500 MHz, CDCl$_3$) 9.00 (s, 1H), 8.11 (dd, J=1.5 Hz, J=7.5 Hz, 2H), 7.50 (m, 3H), 2.75 (s, 3H), 2.36 (m, 1H), 1.77 (m, 2H), 1.66 (m, 2H), 0.96 (t, J=7.5 Hz, 6H); mass spectrum (ES) m/e=381.2 (M+H).

EXAMPLE 6

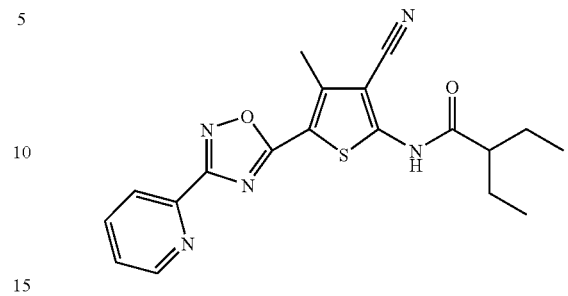

N-[3-Cyano-4-methyl-5-(3-pyridin-2-yl-1,2,4-oxadiazol-5-yl)thien-2-yl]-2-ethylbutanamide. $^1$H NMR (500 MHz, CDCl$_3$) 9.47 (s, 1H), 8.83 (d, J=4.0 Hz, 1H), 8.18 (d, J=8.0 Hz, 1H), 7.91 (m, 1H), 7.44 (m, 1H), 2.73 (s, 3H), 2.43 (m, 1H), 1.75 (m, 2H), 1.65 (m, 2H), 0.94 (t, J=7.5 Hz, 6H); mass spectrum (ES) m/e=382.1 (M+H).

EXAMPLE 7

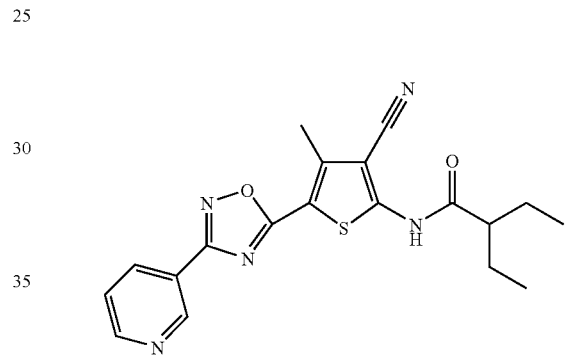

N-[3-Cyano-4-methyl-5-(3-pyridin-3-yl-1,2,4-oxadiazol-5-yl)thien-2-yl]-2-ethylbutanamide. $^1$H NMR (500 MHz, CDCl$_3$) 9.46 (s, 1H), 9.34 (s, 1H), 8.75 (d, J=3.5 Hz, 1H), 8.40 (d, J=3.5 Hz, 1H), 7.45 (dd, J=5.0 Hz, J=8.0 Hz, 1H), 2.74 (s, 3H), 2.42 (m, 1H), 1.75 (m, 2H), 1.66 (m, 2H), 0.96 (t, J=7.0 Hz); mass spectrum (ES) m/e=382.1 (M+H).

EXAMPLE 8

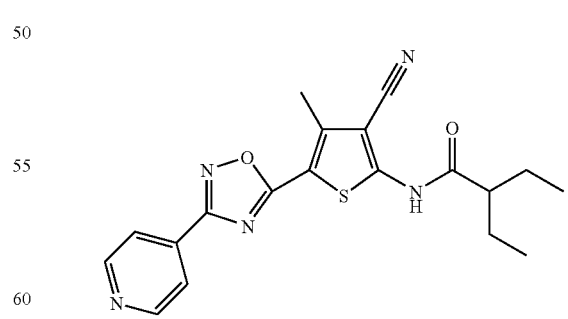

N-[3-Cyano-4-methyl-5-(3-pyridin-4-yl-1,2,4-oxadiazol-5-yl)thien-2-yl]-2-ethylbutanamide. $^1$H NMR (500 MHz, CDCl$_3$) 9.42 (s, 1H), 8.80 (d, 2H), 8.05 (d, 2H), 2.74 (s, 3H), 2.43 (m, 1H) 1.77 (m, 2H), 1.66 (m, 2H), 0.96 (t, J=7.5 Hz, 6H); mass spectrum (ES) m/e=382.1 (M+H).

EXAMPLE 9

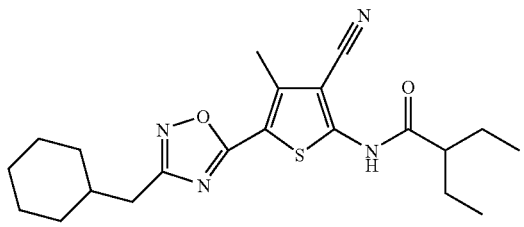

N-{3-Cyano-5-[3-(cyclohexylmethyl)-1,2,4-oxadiazol-5-yl]-4-methylthien-2-yl}-2-ethylbutanamide. $^1$H NMR (500 MHz, CDCl$_3$) 9.15 (s, 1H), 2.66 (s, 3H), 2.61 (d, J=7.0 Hz, 2H), 2.36 (m, 1H), 1.70 (m, 9H), 1.23 (m, 3H), 1.05 (m, 1H), 0.94 (t, J=7.5 Hz, 6H); mass spectrum (ES) m/e=401.3 (M+H).

EXAMPLE 10

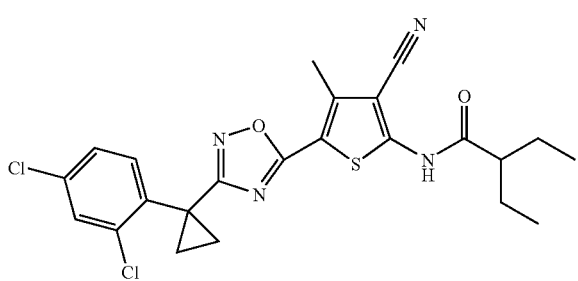

N-(3-Cyano-5-{3-[1-(2,4-dichlorophenyl)cyclopropyl]-1,2,4-oxadiazol-5-yl}-4-methylthien-2-yl)-2-ethylbutanamide. $^1$H NMR (500 MHz, CDCl$_3$) 9.37 (s, 1H), 7.41 (d, J=2.0 Hz, 1H), 7.37 (d, J=8.5 Hz, 1H), 7.23 (dd, J=2.0 Hz, J=8.0 Hz, 1H), 2.60 (s, 3H), 2.38 (m, 1H), 1.79 (m, 2H), 1.73 (m, 2H), 1.61 (m, 2H), 1.39 (dd, J=5.0 Hz, J=9.5 Hz, 2H), 0.94 (t, J=7.5 Hz, 6H); mass spectrum (ES) m/e=489.1 (M+H).

EXAMPLE 11

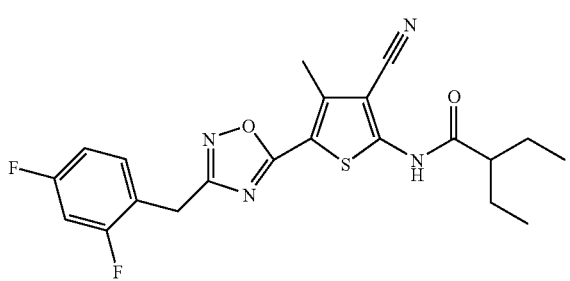

N-[3-Cyano-5-[3-(2,4-difluorobenzyl)-1,2,4-oxadiazol-5-yl]-4-methylthien-2-yl]-2-ethylbutanamide. $^1$H NMR (500 MHz, DMSO-D$_6$) 9.52 (s, 1H), 7.48 (m, 1H), 7.23 (m, 1H), 7.08 (m, 1H), 4.15 (s, 2H), 2.72 (m, 1H), 2.56 (s, 3H), 1.58 (m, 2H), 1.51 (m, 2H), 0.83 (t, J=7.0 Hz, 6H); mass spectrum (ES) m/e=431.1 (M+H).

EXAMPLE 12

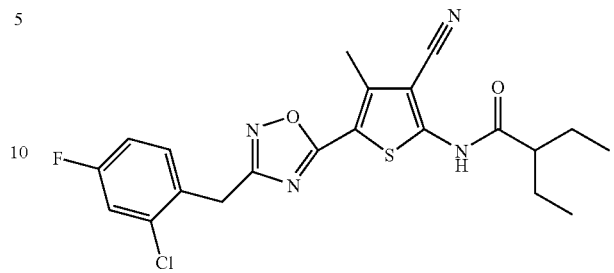

N-{5-[3-(2-Chloro-4-fluorobenzyl)-1,2,4-oxadiazol-5-yl]-3-cyano-4-methylthien-2-yl}-2-ethylbutanamide. $^1$H NMR (500 MHz, DMSO-D$_6$) 9.52 (s, 1H), 7.55 (dd, J=6.5 Hz, J=8.5 Hz, 1H), 7.47 (m, 1H), 7.25 (m, 1H), 4.24 (s, 2H), 2.72 (s, 1H), 2.57 (s, 3H), 1.58 (m, 2H), 1.51 (m, 2H), 0.83 (t, J=8.0 Hz, 6H); mass spectrum (ES) m/e=447.1 (M+H).

EXAMPLE 13

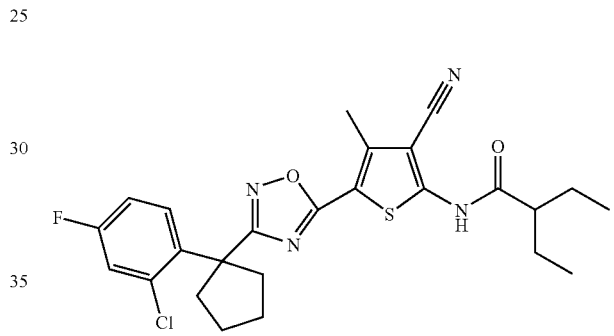

N-(5-{3-[1-(2-Chloro-4-fluorophenyl)cyclopentyl]-1,2,4-oxadiazol-5-yl}-3-cyano-4-methylthien-2-yl)-2-ethylbutanamide. $^1$H NMR (500 MHz, DMSO-D$_6$) 9.43 (s, 1H), 7.70 (m, 1H), 7.38 (dd, J=5.5 Hz, J=9.0 Hz, 1H), 7.26 (m, 1H), 2.71 (m, 1H), 2.60 (m, 2H), 2.50 (s, 3H), 2.23 (m, 2H), 1.77 (m, 4H), 1.56 (d, 2H), 1.51 (m, 2H), 0.82 (t, J=7.5 Hz, 6H); mass spectrum (ES) m/e=501.1 (M+H).

EXAMPLE 14

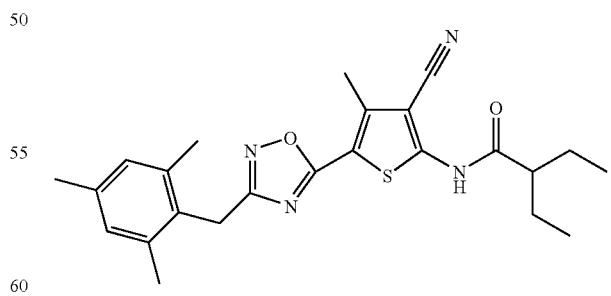

N-{3-Cyano-5-[3-(mesitylmethyl)-1,2,4-oxadiazol-5-yl]-4-methylthien-2-yl}-2-ethylbutanamide. $^1$H NMR (500 MHz, CDCl$_3$/CD$_3$OD) 8.56 (s, 1H), 6.84 (s, 2H), 4.03 (s, 2H), 2.41 (m, 1H), 2.39 (s, 3H), 1;71 (m, 2H), 1.59 (m, 2H), 0.90 (t, J=7.5 Hz, 6H); mass spectrum (ES) m/e=437.2 (M+H).

EXAMPLE 15

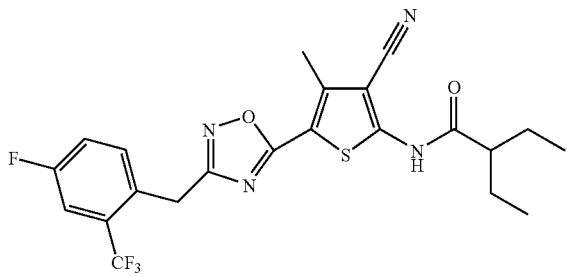

N-(3-Cyano-5-{3-[4-fluoro-2-(trifluoromethyl)benzyl]-1,2,4-oxadiazol-5-yl}-4-methylthien-2-yl)-2-ethylbutanamide. $^1$H NMR (500 MHz, CD$_3$OD) 9.20 (s, 1H), 7.65 (dd, J=5.5 Hz, J=8.5 Hz, 1H), 7.53 (dd, J=3.0 Hz, J=9.5 Hz, 1H), 7.42 (dt, J=2.5 Hz, J=8.5 Hz, 1H), 4.33 (s, 2H), 2.68 (m, 1H), 2.67 (s, 3H), 1.74 (m, 2H), 1.63 (m, 2H), 0.96 (t, J=7.0 Hz, 6H); mass spectrum (ES) m/e=481.1 (M+H).

EXAMPLE 16

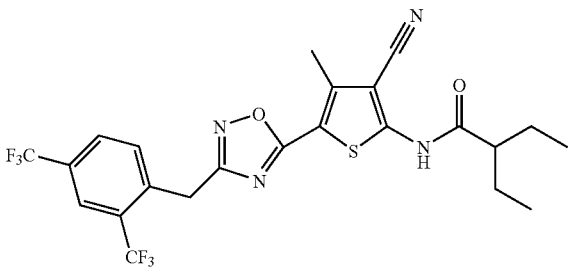

N-(5-{3-[2,4-Bis(trifluoromethyl)benzyl]-1,2,4-oxadiazol-5-yl}-3-cyano-4-methylthien-2-yl)-2-ethylbutanamide. $^1$H NMR (500 MHz, CD$_3$OD) 9.22 (s, 1H), 8.04 (s, 1H), 7.98 (t, J=8.5 Hz, 1H), 7.84 (d, J=8.0 Hz, 1H), 4.46 (s, 2H), 2.67 (s, 3H), 2.66 (m, 1H), 1.73 (m, 2H), 1.63 (m, 2H), 0.96 (t, J=7.0 Hz, 6H); mass spectrum (ES) m/e=531.1 (M+H).

EXAMPLE 17

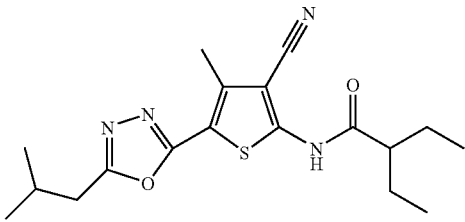

Step A. Methyl 4-cyano-5-[(2-ethylbutanoyl)amino]-3-methylthiophene-2-carboxylate. To a solution of 0.100 g (0.356 mmol) of the intermediate prepared in Preparative Example 2, step A, in 3 mL of methanol was added 0.080 g (0.430 mmol) of EDC. After 16 h at ambient temperature the reaction was diluted with 50 mL of EtOAc, and washed with 50 mL of 1 N aqueous NaHSO$_4$, followed by H$_2$O, and brine. The organic layer was dried (MgSO$_4$) and concentrated in vacuo. Mass spectrum (ES) m/e=295.2 (M+H).

Step B. N-[3-Cyano-5-(hydrazinocarbonyl)-4-methylthien-2-yl]-2-ethylbutanamide. To a solution of 0.105 g (0.356 mmol) of the intermediate prepared in step A in 4 mL of MeOH was added 0.034 mL (1.068 mmol) of hydrazine. The reaction was heated to reflux for 16 h, then cooled to ambient temperature and concentrated in vacuo. The material was re-dissolved in MeOH and concentrated an additional three times, affording the title compound as a white solid. Mass spectrum (ES) m/e=295.2 (M+H).

Step C. N-(3-Cyano-4-methyl-5-{[2-(3-methylbutanoyl)hydrazinolcarbonyl}thien-2-yl)-2-ethylbutanamide. To a solution of 0.105 g (0.356 mmol) of the intermediate prepared in step B in 4 mL of DMF was added 0.039 mL (0.356 mmol) of 3-methylbutanoic acid, followed by 0.096 g (0.712 mmol) of HOBT, and 0.100 g (0.534 mmol) of EDC. After 20 h at ambient temperature the reaction was diluted with 50 mL of CH$_2$Cl$_2$, and washed with saturated aqueous NaHCO$_3$. The organic layer was dried (Na$_2$SO$_4$) and concentrated in vacuo. Purification by flash chromatography (50% EtOAc in hexane) afforded the title compound as a yellow solid. Mass spectrum (ES) m/e=379.2 (M+H).

Step D. N-[3-Cyano-5-(5-isobutyl-1,3,4-oxadiazol-2-yl)-4-methylthien-2-yl]-2-ethylbutanamide. To a solution of 0.042 g (0.110 mmol) of the material prepared in step C in 2 mL of diethylether at 0° C. was added 0.023 nL (0.286 mmol) of pyridine, followed by 0.011 mL (0.144 mmol) of thionyl chloride. After 2 h at 0° C. the mixture was filtered and the solution concentrated in vacuo. The residue was dissolved in 3 mL of toluene and heated to reflux for 1 h, then cooled to ambient temperature and concentrated in vacuo. The residue was purified by preparative thin layer chromatography (20% EtOAc in hexane) affording the title compound as a white solid. $^1$H NMR (500 MHz, CDCl$_3$) 9.04 (s, 1H), 2.76 (d, J=7.0 Hz, 2H), 2.65 (s, 3H), 2.35 (m, 1H), 2.17 (sept., J=6.5 Hz, 1H), 1.73 (m, 2H), 1.64 (m, 2H), 1.02 (d, J=6.5 Hz, 6H), 0.94 (t, J=7.5 Hz, 6H); mass spectrum (ES) m/e=361.2 (M+1).

EXAMPLE 18

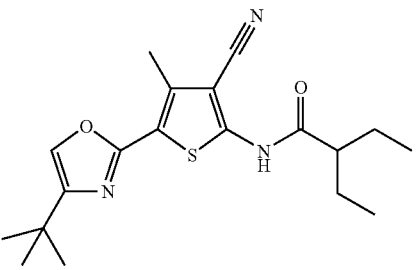

Step A. N-(3-Cyano-5-{[(2,5-dioxopyrrolidin-1-yl)oxy]carbonyl}-4-methylthien-2-yl)-2-ethylbutanamide. To a solution of 0.400 g (1.43 mmol) of the intermediate prepared in Preparative Example 1, step A, in 10 mL of CH$_2$Cl$_2$ was added 0.160 g (1.43 mmol) of N-hydroxysuccinimide, followed by 0.350 g (1.85 mmol) of EDC. After 21 h at ambient temperature the reaction was concentrated in vacuo and dissolved in 50 mL of EtOAc. The organic layer was washed twice with an equal volume of 0.5 N NaHCO$_3$, then brine. The organic layer was dried (MgSO$_4$) and concentrated in vacuo, affording the title compound. Mass spectrum (ES) m/e=378.1 (M+1).

Step B. 4-Cyano-5-[(2-ethylbutanoyl)amino]-3-methylthiophene-2-carboxamide. To a solution of 0.539 g (1.43 mmol) of the intermediate prepared in step A in 8 mL of dioxane was added 0.28 mL (2.15 mmol) of 30% aqueous ammonium hydroxide solution. After 1.5 h at ambient temperature the reaction was filtered and the solid triturated with hexane, affording the title compound as a white solid. Mass spectrum (ES) m/e=280.2 (M+1).

Step C. N-[5-(4-tert-Butyl-1,3-oxazol-2-yl)-3-cyano-4-methylthien-2-yl]-2-ethylbutanamide. To a solution of 0.100 g (0.360 mmol) of the intermediate prepared in step B in 4 mL of DMF was added 0.048 mL (0.360 mmol) of 1-bromo-3,3-dimethylbutan-2-one. The reaction was heated to 85° C. for 4 h, then cooled to ambient temperature and diluted with 30 mL of EtOAc. The organic layer was washed twice with 40 mL of 0.5 N NaHCO$_3$, then brine. The organic layer was dried (MgSO$_4$) and concentrated in vacuo. Purification by preparative thin layer chromatography (10% EtOAc in hexane) afforded the title compound as a white solid. $^1$H NMR (500 MHz, CDCl$_3$) 8.59 (s, 1H), 7.29 (s, 1H), 2.60 (s, 3H), 2.28 (m, 1H), 1.73 (m, 2H), 1.64 (m, 2H), 1.26 (s, 9H), 0.94 (t, J=7.5 Hz, 6H); mass spectrum (ES) m/e=360.2 (M+1).

EXAMPLE 19

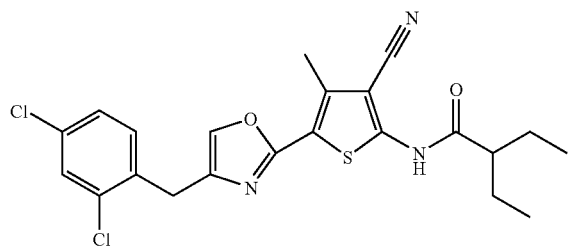

Step A. 2-(2,4-Dichlorophenyl)-N-methoxy-N-methylacetamide. To a solution of 20.50 g (100 mmol) of (2,4-dichlorophenyl)acetic acid in 200 mL of CH$_2$Cl$_2$ was added 12.7 g (130 mmol) of N,O-dimethylhydroxylamine hydrochloride, followed by 17.6 g (130 mmol) of HOBT, 34.8 mL (200 mmol) of di-iso-propylethamine, and 24.9 g (130 mmol) of EDC. After 1.5 h at ambient temperature the reaction was diluted with 500 mL of CH$_2$Cl$_2$ and washed with saturated aqueous NaHCO$_3$. The organic layer was dried (Na$_2$SO$_4$) and concentrated in vacuo. Purification by flash chromatography (33% EtOAc in hexane) afforded the title compound as a clear oil. Mass spectrum (ES) m/e=248.0 (M+1).

Step B. 1-(2,4-Dichlorophenyl)acetone. To a solution of 22.6 g (91.3 mmol) of the intermediate prepared in step A in 100 mL of THF at −78° C. was added 100 mL (140 mmol) of a 1.4 M solution of methylmagnesium bromide in THF/toluene. The reaction was warmed to ambient temperature and stirred for 30 minutes, then cooled to 0° C. and quenched by the addition of saturated aqueous NH4Cl. The mixture was diluted with 200 mL of EtOAc, and the organic layer washed with saturated aqueous NaHCO3, and brine, dried (MgSO4), and concentrated in vacuo. Purification by flash chromatography (10% EtOAc in hexane) afforded the title compound as a white solid. Mass spectrum (ES) m/e=203.0 (M+1).

Step C. 1-Bromo-3-(2,4-dichlorophenyl)acetone. To a solution of 0.500 g (2.46 mmol) of the intermediate prepared in step B in 10 mL of CH$_2$Cl$_2$ at −78° C. was added 0.510 mL (2.95 mmol) of di-iso-propylethylamine, followed by 0.490 mL (2.71 mmol) of trimethylsilyl trifluoromethanesulfonate. After 30 min the reaction was diluted in 100 mL of CH$_2$Cl$_2$ and washed with saturated aqueous NaHCO$_3$. The organic layer was dried (Na$_2$SO$_4$) and concentrated in vacuo. To a solution of 677 mg (2.46 mmol) of this intermediate in 10 mL of THF was added 0.250 g (2.95 mmol) of NaHCO$_3$. The mixture was cooled to 0° C., and 0.440 g (2.46 mmol) of N-bromosuccinimide was added. After warming to ambient temperature and stirring 16 h the mixture was diluted with 50 mL of EtOAc and washed with saturated aqueous NaHCO$_3$ and brine, dried (MgSO$_4$), and concentrated in vacuo. Purification by flash chromatography (33% EtOAc in hexane) afforded the title compound as a colorless oil. $^1$H NMR (500 MHz, CDCl$_3$) 7.40 (s, 1H), 7.23 (m, 1H), 7.18 (d, 1H), 4.06 (s, 2H), 3.94 (s, 2H).

Step D. N-{3-Cyano-5-[4-(2,4-dichlorobenzyl)-1,3-oxazol-2-yl]-4-methylthien-2-yl}-2-ethylbutanamide. The title compound was prepared using the method from Example 18, step C, and using the intermediates prepared in Example 18, step B, and Example 19, step C. Purification by preparative thin layer chromatography afforded the title compound as a yellow solid. $^1$H NMR (500 MHz, DMSO-D$_6$) 7.89 (s, 1H), 7.62 (d, J=1.5 Hz, 1H), 7.41 (m, 2H), 3.96 (s, 2H), 3.23 (s, 3H), 2.67 (m, 1H), 1.57 (m, 2H), 1.49 (m, 2H), 0.83 (t, J=6.5 Hz, 6H); mass spectrum (ES) m/e=462.1 (M+H).

EXAMPLE 20

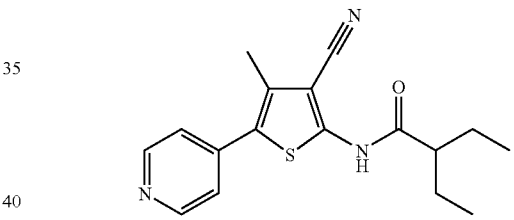

Step A. N-(5-Bromo-3-cyano-4-methylthien-2-yl)-2-ethylbutanamide. To a solution of 0.300 g (1.07 mmol) of the intermediate prepared in Preparative Example 2, step A, in 1.07 mL (1.07 mmol) of a 1 M aqueous solution of AgNO$_3$ was added 1% aqueous NaOH until the solution was pH 7. After 2 h at ambient temperature the precipitate was filtered and dried in vacuo. The solid was then suspended in 10 mL of CCl$_4$, and to this suspension was added 0.073 mL (1.42 mmol) of a 2.0 M solution of Br$_2$ in CCl$_4$. After 22 h at ambient temperature the reaction was diluted with 100 mL of CHCl$_3$ and washed with saturated aqueous NaHCO$_3$. The organic layer was dried (Na$_2$SO$_4$) and concentrated in vacuo. Purification by flash chromatography (10% EtOAc in hexane) afforded the title compound as an off-white solid. $^1$H NMR (500 MHz, CDCl$_3$) 8.83 (s, 1H), 2.28 (m, 1H), 2.24 (s, 3H), 1.76 (m, 2H), 1.62 (m, 2H), 0.96 (t, J=7.5 Hz, 6H); mass spectrum (ES) m/e=317.1 (M+H).

Step B. N-(3-Cyano-4-methyl-5-pyridin-4-ylthien-2-yl)-2-ethylbutanamide. To a solution of 0.050 g (0.160 mmol) of the intermediate prepared in step A in 2 mL of DMF was added 0.016 g (0.13 mmol) of pyridin-4-ylboronic acid, 0.13 mL (0.26 mmol) of 2 M aqueous Na$_2$CO$_3$ solution, followed by 0.009 g (0.008 mmol) of tetrakis(triphenylphosphine) palladium (0). The mixture was heated to 70° C. for 2 h, then cooled to ambient temperature. The mixture was diluted with EtOAc, and washed with 0.5 M NaHCO₃ and brine, dried (MgSO₄) and concentrated in vacuo. Purification by preparative thin layer chromatography (33% EtOAc in hexane) afforded the title compound as a white solid. ¹H NMR (500 MHz, CDCl₃) 8.95 (s, 1H), 8.64 (d, J=5.0 Hz, 2H), 7.39 (d, J=6.5 Hz, 2H), 2.43 (s, 3H), 2.34 (m, 1H), 1.74 (m, 2H), 1.63 (m, 2H), 0.94 (t, J=7.5 Hz, 6H); mass spectrum (ES) m/e=314.2 (M+H).

EXAMPLE 21

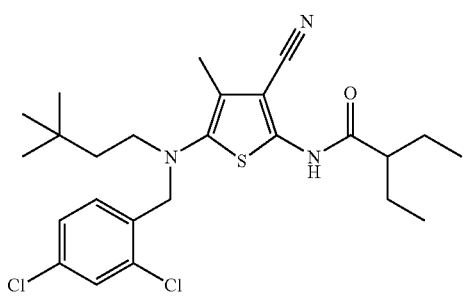

Step A. tert-Butyl 4-cyano-5-[(2-ethylbutanoyl)amino]-3-methylthien-2-ylcarbamate. To a solution of 1.00 g (3.57 mmol) of the intermediate prepared in Preparative Example 2, step A, in 30 mL of toluene was added 1.00 mL (7.14 mmol) of triethylamine, followed by 0.924 mL (4.30 mmol) of diphenylphosphorylazide. After 4.5 h at ambient temperature the reaction was concentrated in vacuo, and the residue was diluted with 200 mL of EtOAc. The mixture was washed with brine, dried (MgSO₄), and concentrated in vacuo, affording a yellow solid. This material was dissolved in 100 mL of tert-butanol. To this solution was added 0.500 μL of triethylamine, and the solution was heated to 92° C. for 16 h. The solution was then concentrated in vacuo and the residue was diluted with 200 mL of EtOAc. The mixture was washed with saturated aqueous NaHCO₃ and brine, dried (MgSO₄) and concentrated in vacuo. Purification by flash chromatography (9% EtOAc in hexane) afforded the title compound as a colorless oil. ¹H NMR (500 MHz, CDCl₃) 9.23 (s, 1H), 6.41 (s, 1H), 2.34 (m, 1H), 2.14 (s, 3H), 1.74 (m, 2H), 1.61 (m, 2H), 1.56 (s, 9H), 0.94 (t, J=7.0 Hz, 6H); mass spectrum (ES) m/e=374.1 (M+Na).

Step B. N-(5-Amino-3-cyano-4-methylthien-2-yl)-2-ethylbutanamide. To a solution of 0.329 g (0.937 mmol) of the intermediate prepared in Step A in 8 mL of CH₂Cl₂ was added 2 mL of trifluoromethanesulfonic acid. After 2 h at ambient temperature the reaction was washed with water, and the mixture was freeze-dried overnight, affording the title compound as a white solid TFA salt. Mass spectrum (ES) m/e=252.2 (M+H).

Step C. N-{3-Cyano-5-[(3,3-dimethylbutyl)amino]-4-methylthien-2-yl}-2-ethylbutanamide. To a solution of 30.0 mg (0.31 mmol) of the intermediate prepared in step B in 2 mL of dichloroethane was added 0.040 mL (0.31 mmol) of 3,3-dimethylbutanal, followed by 0.044 mL (0.775 mmol) of acetic acid, and 0.131 g (0.775 mmol) of sodium triacetoxyborohydride. After 4 h at ambient temperature the reaction was diluted with 50 mL of CH₂Cl₂ and washed with saturated NaHCO₃. The organic layer was dried (Na₂SO₄) and concentrated in vacuo. Purification by flash chromatography (9.5% EtOAc in hexane) afforded the title compound as a yellow powder. Mass spectrum (ES) m/e=336.2 (M+H).

Step D. N-{3-Cyano-5-[(2,4-dichlorobenzyl)(3,3-dimethylbutyl)amino]-4-methylthien-2-yl}-2-ethylbutanamide. To a solution of 0.052 mg (0.165 mmol) of the intermediate from step C in 3 mL of dichloroethane was added 0.068 g (0.390 mmol) of 2,4-dichlorobenzaldehyde, followed by 0.044 mL (0.775 mmol) of acetic acid, and 0.082 g (0.390 mmol) of sodium triacetoxyborohydride. After 16 h at ambient temperature the reaction was diluted with 50 mL of CH₂Cl₂ and washed with saturated aqueous NaHCO₃. The organic layer was dried (Na₂SO₄) and concentrated in vacuo. Purification by preparative thin layer chromatography (10% EtOAc in hexane) afforded the title compound as a white solid. ¹H NMR (500 MHz, CDCl₃) 8.88 (s, 1H), 7.38 (d, J=2.0 Hz, 1H), 7.21 (m, 2H), 4.09 (s, 2H), 2.97 (m, 2H), 2.98 (m, 1H), 1.96 (s, 3H), 1.76 (m, 2H), 1.63 (m, 2H), 1.40 (m, 2H), 0.97 (t, J=7.5 Hz, 6H), 0.87 (s, 9H); mass spectrum (ES) m/e=494.1 (M+H).

Using the intermediate prepared in Example 21 step B and the procedures from Example 21, step C and D, the following compounds were prepared.

EXAMPLE 22

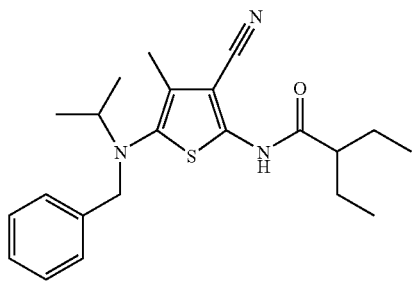

N-{5-[Benzyl(isopropyl)amino]-3-cyano-4-methylthien-2-yl}-2-ethylbutanamide. ¹H NMR (500 MHz, CDCl₃) 8.95 (s, 1H), 7.25 (m, 5H), 4.06 (s, 2H), 3.30 (m, 1H), 2.30 (m, 1H), 2.00 (s, 3H), 1.74 (m, 2H), 1.62 (m, 2H), 1.17 (d, J=6.5 Hz, 6H), 0.96 (t, J=7.5 Hz, 6H); mass spectrum (ES) m/e=384.2 (M+1).

EXAMPLE 23

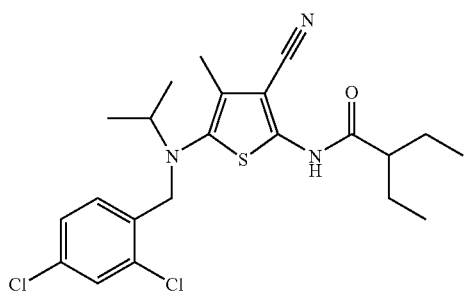

N-{3-Cyano-5-[(2,4-dichlorobenzyl)(isopropyl)amino]-4-methylthien-2-yl}-2-ethylbutanamide. ¹H NMR (500 MHz, CDCl₃) 8.89 (s, 1H), 7.35 (d, J=1.0 Hz, 1H), 7.11 (m, 2H), 4.11 (s, 2H), 3.65 (sept., J=6.5 Hz, 1H), 2.29 (m, 1H), 1.90 (s, 3H), 1.76 (m, 2H), 1.62 (m, 2H), 1.18 (d, J=7.0 Hz, 6H), 0.97 (t, J=7.5 Hz, 6H); mass spectrum (ES) m/e=452.1 (M+H).

EXAMPLE 24

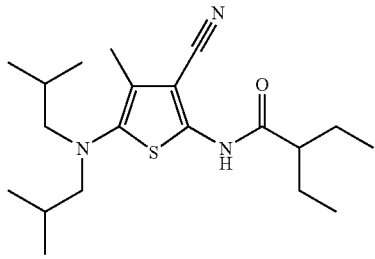

N-[3-Cyano-5-(diisobutylamino)-4-methylthien-2-yl]-2-ethylbutanamide. $^1$H NMR (500 MHz, CDCl$_3$) 8.98 (s, 1H), 2.62 (d, J=7.5 Hz, 4H), 2.30 (m, 1H), 2.19 (s, 3H), 1.73 (m, 2H), 1.68 (m, 2H), 1.62 (m, 2H), 0.96 (t, J=7.5 Hz, 6H), 0.91 (d, J=7.0 Hz, 12H); mass spectrum (ES) m/e=364.2 (M+H).

EXAMPLE 25

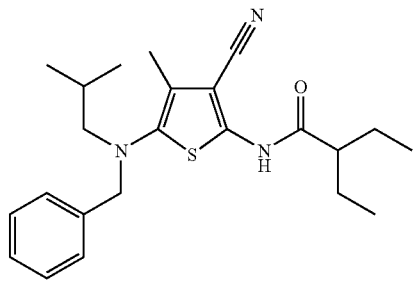

N-{5-[Benzyl(isobutyl)amino]-3-cyano-4-methylthien-2-yl}-2-ethylbutanamide. $^1$H NMR (500 MHz, CDCl$_3$) 8.83 (s, 1H), 7.30 (m, 5H), 3.97 (s, 2H), 2.69 (d, J=7.0 Hz, 2H), 2.29 (m, 1H), 2.05 (s, 3H), 1.73 (m, 2H), 1.64 (m, 2H), 0.97 (t, J=7.5 Hz, 6H), 0.90 (d, J=6.5 Hz, 6H); mass spectrum (ES) m/e=398.3 (M+H).

EXAMPLE 26

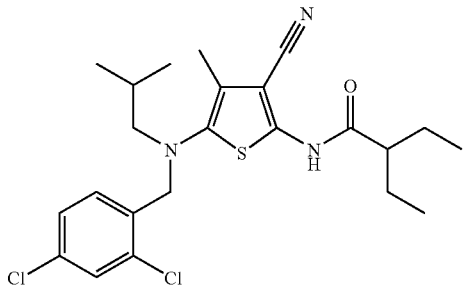

N-{3-Cyano-5-[(2,4-dichlorobenzyl)(isobutyl)amino]-4-methylthien-2-yl}-2-ethylbutanamide. $^1$H NMR (500 MHz, CDCl$_3$) 8.92 (s, 1H), 7.40 (s, 1H), 7.18 (s, 2H), 4.05 (s, 2H), 2.76 (d, J=7.0 Hz, 2H), 2.29 (m, 1H), 1.91 (s, 3H), 1.73 (m, 3H), 1.62 (m, 2H), 0.97 (t, J=7.0 Hz, 6H), 0.92 (d, J=6.5 Hz, 6H); mass spectrum (ES) m/e=466.2 (M+H).

EXAMPLE 27

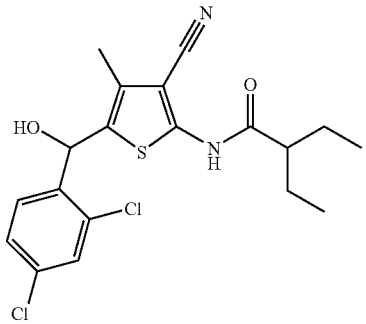

N-{3-Cyano-5-[(2,4-dichlorophenyl)(hydroxy)methyl]-4-methylthien-2-yl}-2-ethylbutanamide. To a solution of 0.042 g (0.133 mmol) of the intermediate prepared in Example 20, step A, in 1 mL of THF at −78° C. was added 0.188 mL (0.200 mmol) of a 1.6 M solution of n-butyllithium in hexane. After 30 min at −78° C., to the solution was added 0.0473 g (0.270 mmol) of 2,4-dichlorobenzaldehyde. After 2 h at −78° C. the reaction was quenched by the addition of 10 mL of saturated aqueous NH$_4$Cl. The mixture was extracted with Et$_2$O and washed with brine, dried (MgSO$_4$) and concentrated in vacuo. Purification by flash chromatography (10% EtOAc in hexane) afforded the title compound as a white solid. $^1$H NMR (500 MHz, CDCl$_3$) 8.82 (s, 1H), 7.73 (d, J=8.0 Hz, 1H), 7.38 (d, J=2.0 Hz, 1H), 7.35 (dd, J=2.0 Hz, J=8.5 Hz, 1H), 6.32 (s, 1H), 2.52 (s, 1H), 2.36 (s, 3H), 2.28 (m, 1H), 1.72 (m, 2H), 1.62 (m, 2H), 0.93 (t, J=7.5 Hz, 3H), 0.93 (t, J=7.5 Hz, 3H); mass spectrum (ES) m/e=411.1 (M+H).

EXAMPLE 28

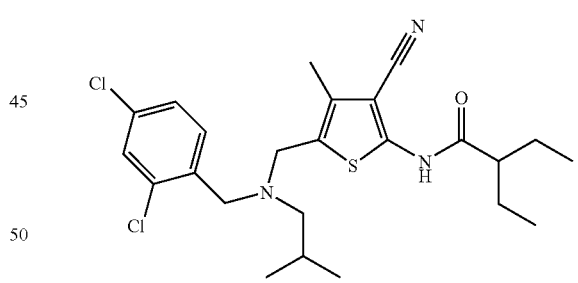

Step A. N-(3-Cyano-5-formyl-4-methylthien-2-yl)-2-ethylbutanamide. To a solution of 0.126 g (0.400 mmol) of the intermediate prepared in Example 20, step A, in 3 mL of THF at −78° C. was added 0.50 mL (0.800 mmol) of a 1.6 M solution of n-butyllithium in hexane. After 30 min at −78° C. to the solution was added 0.062 mL (0.800 mmol) of DMF, and the solution was warmed slowly to ambient temperature. After 1.5 h at ambient temperature the solution was quenched by the addition of saturated aqueous NH$_4$Cl. The mixture was extracted with Et$_2$O, and the organic layer was washed with brine, dried (MgSO$_4$) and concentrated in vacuo. Purification by flash chromatography (25% EtOAc in hexane) afforded the title compound as a colorless oil. $^1$H NMR (500 MHz, CDCl$_3$) 10.01 (s, 1H), 9.23 (s, 1H), 2.64

(s, 3H), 2.42 (m, 1H), 1.76 (m, 2H), 1.62 (m, 2H), 0.92 (t, J=7.0 Hz, 6H); mass spectrum (ES) m/e=265.2 (M+H).

Step B. N-(3-Cyano-5-{[(2,4-dichlorobenzyl)(isobutyl) amino]methyl}-4-methylthien-2-yl)-2-ethylbutanamide. To a solution of 0.063 g (0.24 mmol) of the intermediate prepared in step A in 8 mL of dichloroethane was added 0.072 mL (0.72 mmol) of isobutylamine, followed by 0.070 mL (1.20 mmol) of acetic acid, and 0.050 g (0.60 mmol) of sodium triacetoxyborohydride. After 18 h at ambient temperature the reaction was diluted with dichloromethane, then quenched with saturated aqueous NaHCO$_3$. The organic layer was dried (Na$_2$SO$_4$) and concentrated in vacuo. This material was then dissolved in 8 mL of dichloroethane, and to this solution was added 0.126 g (0.700 mmol) of 2,4-dichlorobenzaldehyde, followed by 0.083 nL (1.45 mmol) of acetic acid, and 148 mg (0.700 mmol) of sodium triacetoxyborohydride. After 16 h at ambient temperature the reaction was diluted with CH$_2$Cl$_2$ and washed with saturated aqueous NaCO$_3$. The organic layer was dried (Na$_2$SO$_4$) and concentrated in vacuo. Purification by flash chromatography (4% EtOAc in hexane) afforded the title compound as a white solid. $^1$H NMR (500 MHz, CDCl$_3$) 9.13 (s, 1H), 7.63 (d, J=8.0 Hz, 1H), 7.33 (d, J=2.0 Hz, 1H), 7.27 (dd, J=2.5 Hz, J=8.5 Hz, 1H), 3.63 (s, 2H), 3.59 (s, 2H), 2.36 (m, 1H), 2.22 (d, J=7.5 Hz, 1H), 2.20 (s, 3H), 1.85 (m, 1H), 1.77 (m, 2H), 1.63 (m, 2H), 0.97 (t, J=8.0 Hz, 6H), 0.90 (d, J=6.5 Hz, 6H); mass spectrum (ES) m/e=502.0 (M+Na).

EXAMPLE 29

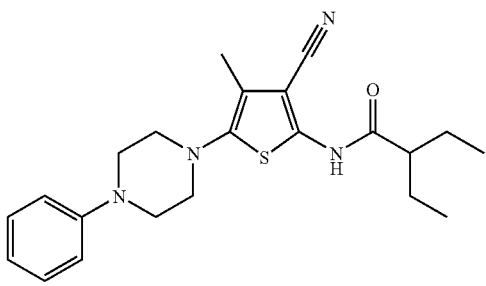

Step A. Ethyl 2-amino-4-methyl-5-(4-phenylpiperazin-1-yl)thiophene-3-carboxylate. To a solution of 0.300 g (2.00 mmol) of phenyloxyacetone in 10 mL of EtOH was added 0.226 mL (2.00 mmol) of ethylcyanoacetate, 0.422 g (2.00 mmol) of 1-phenylpiperazine, and 64 mg (0.200 mmol) of elemental sulfur. After 18 h at 100° C. the reaction was cooled to ambient temperature and concentrated to dryness. The residue was purified by flash chromatography (10% EtOAc in hexane) affording the title compound as a white solid. $^1$H NMR (500 MHz, CDCl$_3$) 7.30 (t, J=7.5 Hz, 2H), 6.98 (d, J=8.0 Hz, 2H), 6.91 (t, J=7.0 Hz, 1H), 6.04 (s, 2H), 4.30 (q, J=7.0 Hz, 2H), 3.31 (t, J=5.0 Hz, 4H), 2.96 (t, J=5.0 Hz, 4H), 2.27 (s, 3H), 1.37 (t, J=7.0 Hz, 3H); mass spectrum (ES) m/e=346.1 (M+H).

Step B. Ethyl 2-[(2-ethylbutanoyl)amino]-4-methyl-5-(4-phenylpiperazin-1-yl)thiophene-3-carboxylate. To a solution of 1.50 g (4.35 mmol) of the intermediate prepared in step A in 20 mL of CH$_2$Cl$_2$ was added 1.134 mL (6.52 mmol) of di-iso-propylethamine, followed by 0.720 mL (5.21 mmol) of 2-ethylbutanoyl chloride. After 18 h at ambient temperature the reaction was quenched by the addition of 20 mL of saturated aqueous NaHCO$_3$. The organic layer was dried (Na$_2$SO$_4$) and concentrated in vacuo. Purification by flash chromatography (10% EtOAc in hexane) afforded the title compound as a colorless oil. $^1$H NMR (500 MHz, CDCl$_3$) 11.47 (s, 1H), 7.31 (t, J=9.0 Hz, 2H), 6.90 (d, J=8.0 Hz, 2H), 6.91 (t, J=7.0 Hz, 1H), 4.38 (q, J=7.0 Hz, 2H), 3.33 (t, J=5.0 Hz, 4H), 3.08 t, J=4.5 Hz, 4H), 2.33 (s, 3H), 2.24 (m, 1H), 1.76 (m, 2H), 1.64 (m, 2H), 1.43 (t, J=7.0 Hz, 3H), 0.964 (t, J=7.5 Hz, 6H); mass spectrum (ES) m/e=444.2 (M+H).

Step C. 2-[(2-Ethylbutanoyl)amino]-4-methyl-5-(4-phenylpiperazin-1-yl)thiophene-3-carboxamide. To a solution of 2.0 g (4.5 mmol) of the intermediate prepared in step B in 25 mL of THF was added 10 mL of MeOH, followed by 10 mL of 1 M aqueous LiOH. After 18 h at ambient temperature the reaction was brought to neutral pH with 6 N aqueous HCl. The reaction was concentrated in vacuo, and the residue was diluted with water and extracted with EtOAc. The organic layer was dried (MgSO$_4$) and concentrated in vacuo. Purification by flash chromatography (50% EtOAc in hexane) afforded the thiophene-3-carboxylate as a yellow solid. To a solution of 0.900 g (2.17 mmol) of this material in 5 mL of CH$_2$Cl$_2$ was added 0.300 g (2.60 mmol) of N-hydroxysuccinimide, followed by 0.500 g (2.60 mmol) of EDC. After 2 h at ambient temperature the reaction was concentrated in vacuo and the residue dissolved in EtOAC and washed with saturated aqueous NaHCO$_3$. The organic layer was then washed with brine, dried (MgSO$_4$) and concentrated in vacuo, affording the thiophene-3-succinate ester as an orange solid. This material was dissolved in 10 mL of dioxane, and to this solution was added 0.380 mL (3.25 mmol) of a 30% aqueous solution of ammonium hydroxide. After 3 h at ambient temperature the liquid was filtered and concentrated in vacuo. Purification of the residue by flash chromatography (30% EtOAc in hexane) afforded the title compound as a white solid. $^1$H NMR (500 MHz, CDCl$_3$) 12.21 (s, 1H), 7.29 (t, J=7.5 Hz, 2H), 6.97 (d, J=8.0 Hz, 2H), 6.89 (t, J=7.0 Hz, 1H), 6.10 (m, 2H), 3.31 (t, J=5.0 Hz, 4H), 3.07 (t, J=4.5 Hz, 4H), 2.41 (s, 3H), 2.23 (m, 1H), 1.72 (m, 2H), 1.61 (m, 2H), 0.95 (t, J=7.0 Hz, 6H); mass spectrum (ES) m/e=415.2 (M+H).

Step D. N-[3-Cyano-4-methyl-5-(4-phenylpiperazin-1-yl)thien-2-yl]-2-ethylbutanamide. To a solution of 0.200 g (0.48 mmol) of the intermediate prepared in step C in 3 mL of DMF was added 0.13 g (0.72 mmol) of cyanuric chloride. After 1 h at ambient temperature the reaction was poured onto 50 mL of saturated aqueous NaHCO$_3$ and extracted with EtOAc. The organic layer was washed with brine, dried (MgSO$_4$) and concentrated in vacuo. Purification by flash chromatography (20% EtOAc in hexane) afforded the title compound as a white solid. $^1$H NMR (500 MHz, CDCl$_3$) 9.001 (s, 1H), 7.305 (t, J=8.0 Hz, 2H), 6.97 (d, J=8.5 Hz, 2H), 6.91 (t, J=7.5 Hz, 1H), 3.31 (t, J=4.5 Hz, 4H), 3.07 (t, J=5.0 Hz, 4H), 2.33 (m, 1H), 2.22 (s, 3H), 1.77 (m, 2H), 1.63 (m, 2H), 0.97 (t, J=7.5 Hz,); mass spectrum (ES) m/e=397.2 (M+H).

EXAMPLE 30

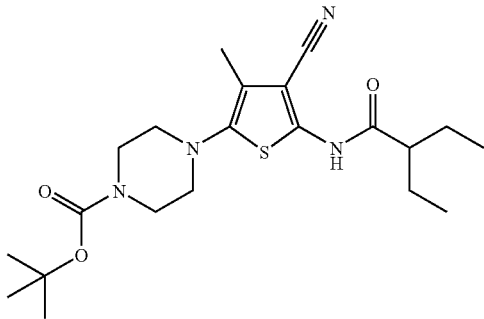

tert-Butyl 4-{4-cyano-5-[(2-ethylbutanoyl)amino]-3-methylthien-2-yl}piperazine-1-carboxylate. The title compound was prepared using the procedure from Example 29, and tertbutylpiperazine-1-carboxylate. $^1$H NMR (500 MHz, CDCl$_3$) 9.27 (s, 1H), 3.53 (s, 4H), 2.83 (s, 4H), 2.34 (m, 1H), 2.17 (s, 3H), 1.73 (m, 2H), 1.59 (m, 2H), 1.48 (s, 9H), 0.94 (t, J=7.5 Hz, 6H); mass spectrum (ES) m/e=443.2 (M+Na).

EXAMPLE 31

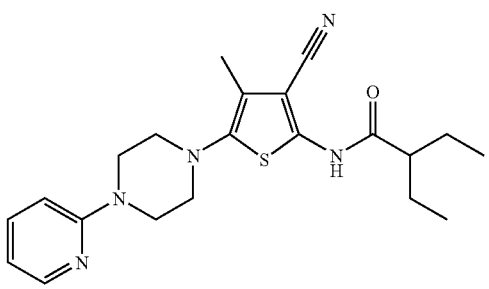

N-[3-Cyano-4-methyl-5-(4-pyridin-2-ylpiperazin-1-yl)thien-2-yl]-2-ethylbutanamide. The title compound was prepared using the procedure from example 29 and 1-pyridin-2-ylpiperazine. $^1$H NMR (500 MHz, CDCl$_3$) 8.98 (s, 1H), 8.21 (dd, J=1.5 Hz, J=5.0 Hz, 1H), 7.51 (m, 1H), 6.67 (m, 2H), 3.66 (t, J=4.5 Hz, 4H), 3.01 (t, J=5.0 Hz, 4H), 2.30 (m, 1H), 2.21 (s, 3H), 1.73 (m, 2H), 1.61 (m, 2H), 0.95 (t, J=7.5 Hz, 6H); mass spectrum (ES) m/e=398.2 (M+H).

EXAMPLE 32

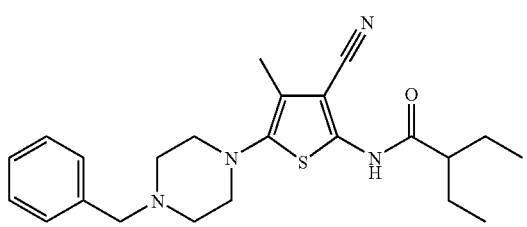

N-[5-(4-Benzylpiperazin-1-yl)-3-cyano-4-methylthien-2-yl]-2-ethylbutanamide. To a solution of 1.06 g (2.52 mmol) of the title compound from Example 30 in 10 mL of CH$_2$Cl$_2$ was added 10 mL of trifluoroacetic acid. After 2 h at ambient temperature the reaction was concentrated in vacuo. To 0.040 g (0.092 mmol) of this intermediate in 1 mL of dichloroethane was added 0.032 mL (0.20 mmol) of benzaldehyde, followed by 0.066 g (0.31 mmol) of sodium triacetoxyborohydride. After 16 h at ambient temperature the reaction was quenched by the addition of 10 mL of saturated aqueous NaHCO$_3$. The reaction was extracted with CH$_2$Cl$_2$ and the organic layer was dried (Na$_2$SO$_4$) and concentrated in vacuo. Purification by preparative thin layer chromatography (15% EtOAc in hexane) afforded the title compound as a white solid. $^1$H NMR (500 MHz, CDCl$_3$) 8.69 (s, 1H), 7.35 (m, 5H), 3.72 (s, 1H), 3.57 (s, 1H), 2.94 (t, J=5.0 Hz, 4H), 2.58 (s, 4H), 2.26 (m, 1H), 2.16 (s, 3H), 1.73 (m, 2H), 1.61 (m, 2H), 0.95 (t, J=7.5 Hz, 6H); mass spectrum (ES) m/e=411.2 (M+H).

EXAMPLE 33

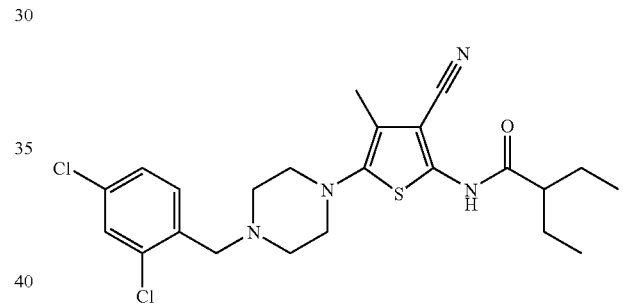

N-{3-Cyano-5-[4-(2,4-dichlorobenzyl)piperazin-1-yl]-4-methylthien-2-yl}-2-ethylbutanamide. To a solution of 1.06 g (2.52 mmol) of the title compound from Example 30 in 10 mL of CH$_2$Cl$_2$ was added 10 mL of trifluoroacetic acid. After 2 h at ambient temperature the reaction was concentrated in vacuo. To 0.040 g (0.092 mmol) of this intermediate in 1 mL of dichloroethane was added 0.055 g (0.20 mmol) of 2,4-dichlorobenzaldehyde, followed by 0.066 g (0.31 mmol) of sodium triacetoxyborohydride. After 16 h at ambient temperature the reaction was quenched by the addition of 10 mL of saturated aqueous NaHCO$_3$. The reaction was extracted with CH$_2$Cl$_2$ and the organic layer was dried (Na$_2$SO$_4$) and concentrated in vacuo. Purification by preparative thin layer chromatography (15% EtOAc in hexane) afforded the title compound as a white solid. $^1$H NMR (500 MHz, CDCl$_3$) 8.79 (s, 1H), 7.45 (d, J=8.5 Hz, 1H), 7.38 (d, J=2.0 Hz, 1H), 7.25 (dd, J=2.0 Hz, J=8.5 Hz, 1H), 3.64 (s, 2H), 2.94 (t, J=4.5 Hz, 4H), 2.63 (t, J=4.5 Hz, 4H), 2.28 (m, 1H), 2.16 (s, 3H), 1.73 (m, 2H), 1.61 (m, 2H), 0.95 (t, J=7.5 Hz, 6H); mass spectrum (ES) m/e=479.1 (M+H).

EXAMPLE 34

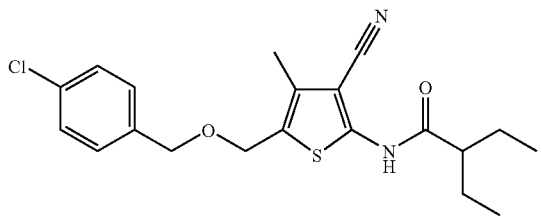

Step A. N-[3-Cyano-5-(hydroxymethyl)-4-methylthien-2-yl]-2-ethylbutanamide. To a solution of 0.110 g (0.390 mmol) of the intermediate prepared in Preparative Example 2, step A, in 3 mL of THF was added 1.92 mL (1.92 mmol) of a 1 M solution of borane in THF. After 2 h at ambient temperature the reaction was cooled to 0° C. and quenched by the slow addition of water. The mixture was extracted with $CH_2Cl_2$, and the organic layer was washed with saturated aqueous $NaHCO_3$, dried ($Na_2SO_4$) and concentrated in vacuo. Purification by preparative reversed phase HPLC afforded the alcohol as a white solid. Mass spectrum (ES) m/e=267.2 (M+H).

Step B. N-(5-{[(4-Chlorobenzyl)oxy]methyl}-3-cyano-4-methylthien-2-yl)-2-ethylbutanamide. To a solution of 0.070 g (0.263 mmol) of the intermediate prepared in step A in 2 mL of DMF was added 0.0483 mg (0.300 mmol) of 1-chloro-4-(chloromethyl)benzene, followed by a catalytic amount of KI, and 0.024 g (0.30 mmol) of a 30% dispersion of NaH in mineral oil. After 18 h at ambient temperature the reaction was quenched by the slow addition of saturated aqueous $NaHCO_3$. The mixture was diluted with 100 mL of EtOAc and washed with 0.5 M $NaHCO_3$ and brine, dried ($MgSO_4$) and concentrated in vacuo. Purification by preparative reversed phase HPLC afforded the title compound as a white solid. $^1H$ NMR (500 MHz, $CDCl_3$) 8.49 (s, 1H), 7.36 (m, 4H), 4.56 (s, 2H), 4.55 (s, 2H), 2.28 (m, 1H), 2.27 (s, 3H), 1.77 (m, 2H), 1.68 (m, 2H), 0.98 (t, J=7.3 Hz, 6H); mass spectrum (ES) m/e=391.1 (M+H).

Biological Assays

The ability of the compounds of the present invention to inhibit the binding of glucagon can be demonstrated using the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765–9(1997); Cascieri et al. *J Biol Chem* 274, 8694–7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM $MgCl_2$, 2 mM EDTA, 12% Glycerol, and 0.200 mg WGA coated PVT SPA beads (Amersham), +/− compounds or 0.001 mM unlabeled glucagon. After 4–12 hours incubation at room temperature, the radioactivity bound to the cell membranes was determined in a radioactive emission detection counter (Microbeta-Wallace). Data was analyzed using the software program Prism® from GraphPad. The $IC_{50}$ were calculated using non-linear regression analysis assuming single site competition.

High Throughput Screening (HTS) Protocol for Glucagon Receptor Binding Assay

Another form of the binding assay was developed suitable for high-throughput screening for modulators of receptor activity. Fully automated or semi-automated protocols and robotic and workstation instruments were utilized for the HTS assay as would be recognized by those practiced in the art. In a typical configuration of the assay, 0.002 mg of cell membrane (as described above) were preincubated with 0.200 mg of WGA-coated PVT beads in buffer containing 100 mM Tris-HCl pH 7.5, 10 mM $MgCl_2$, 4 mM EDTA, 24% Glycerol, and 0.2% BSA. The membrane/bead mixture was then dispensed (0.050 mL) into each well of 96-well plates (Wallac Isoplates, white clear bottom) containing 0.100 mL of test compounds or control solutions. A second addition (0.050 mL) was then dispensed into the wells of the plate containing 125]-Glucagon (approximately 25,000 CPM). The solutions were dispensed using a Multidrop Stacker 20 (Titertek) liquid dispenser. An adhesive plate seal (Packard) was applied and the plates were shaken for 5 minutes. The plates were further incubated at ambient temperature for several hours for establishment of equilibrium (typically 5 hours) and the signal was stable for up to three days. The plates were read in a scintillation counter (Wallac Microbeta) for 1 min/well. Activity of test compounds was calculated by comparing to the total scintillation signal (CPM) of control samples with no compound and with 0.001 mM unlabeled-glucagon.

Inhibition of Glucagon-stimulated Intracellular cAMP Formation

Exponentially growing CHO cells expressing human glucagon receptor were harvested with the aid of enzyme-free dissociation media (Specialty Media), pelleted at low speed, and re-suspended in cell suspension buffer [75 mM Tris-HCl pH7.5, 250 mM Sucrose, 25 mM $MgCl_2$, 1.5 mM EDTA, 0.1 mM Ro-20-1724 (Biomol, Inc.), 0.2% bovine serum albumin and one tablet of completed™ (Boehringer), which contains a cocktail of protease inhibitors, for each 50 ml of buffer]. An adenylate cyclase assay was setup using an Adenylate Cyclase Assay kit (SMP-004B) from New England Nuclear (NEN) as per manufacturer instructions. Briefly, compounds were diluted from stocks in a cell stimulation buffer supplied with the kit. Cells prepared as above were preincubated in flash plates coated with anti-cAMP antibodies (NEN) in presence of compounds or DMSO controls for 40 minutes, and then stimulated with glucagon (250 pM) for an additional 40 minutes. The cell stimulation was stopped by addition of equal amount of a detection buffer containing lysis buffer as well as $^{125}$I-labeled cAMP tracer (NEN). After 3–6 h of incubation at room temperature the bound radioactivity was determined in a liquid scintillation counter (TopCount-Packard Instruments). Activity of test compounds was calculated by comparing to the total scintillation signal (CPM) of control samples with no compound and with 0.001 mM unlabeled-glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

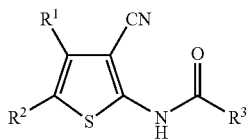

or a pharmaceutically acceptable salt or solvate thereof wherein:

$R^1$ is selected from the group consisting of: H, $C_{1-10}$alkyl, Aryl, Heteroaryl and Heterocyclyl, said alkyl, Aryl, Heteroaryl and Heterocyclyl being optionally substituted with one to four substituents independently selected from $R^6$;

$R^2$ represents $NR^4R^5$, $R^3$ is selected from the group consisting of: $C_{1-10}$alkyl and Aryl, said alkyl and Aryl being optionally substituted with one to four substituents independently selected from $R^6$;

$R^4$ is selected from H and $C_{1-10}$alkyl, $R^5$ is $C_{1-10}$alkyl having 1–2 $R^6$ groups attached;

$R^6$ is independently selected from the group consisting of halo, $C_{1-7}$alkyl, Aryl, Heteroaryl, Heterocyclyl, $OR^7$, $SR^7$, $S(O)_mR^8$, $S(O)_2OR^8$, $S(O)_mNR^7R^8$, $NO_2$, $NR^7R^8$, $O(CR^9R^{10})_nNR^7R^8$, $C(O)R^8$, $CO_2R^7$, $CO_2(CR^9R^{10})_n$ $CONR^7R^8$, $OC(O)R^8$, CN, $C(O)NR^7R^8$, $NR^7C(O)R^8$, $OC(O)NR^7R^8$, $NR^7C(O)OR^8$, $NR^7C(O)NR^8R^9$, $CR^7(NOR^8)$, $(CR^9R^{10})_n$-Aryl, $(CR^9R^{10})_n$-Heteroaryl, $(CR^9R^{10})_n$-Heterocyclyl, $CF_3$ and $OCF_3$;

wherein m is 0, 1 or 2 and n is an integer from 1 to 7, and the alkyl, Heterocyclyl, Aryl and Heteroaryl groups and portions are optionally substituted with 1–4 substituents selected from a group independently selected from $R^{11}$;

$R^7$, $R^9$ and $R^{10}$ are independently selected from the group consisting of: H, $C_{1-7}$alkyl, Aryl, Ar—$C_{1-10}$alkyl and mono-, di- and tri- halo substituted Ar—$C_{1-10}$alkyl, or one $R^9$ and one $R^{10}$ are taken together with the atoms to which they are attached and any intervening atoms and represent a ring of 3 to 8 members containing 0–2 heteroatoms independently selected from 0, S and N;

$R^8$ is selected from the group consisting of: $C_{1-10}$alkyl, Aryl and $C_{1-10}$alkyl-Aryl; and $R^{11}$ is selected from the group consisting of: halo, CN, $C_{1-4}$alkyl, Aryl, $CF_3$ and OH.

2. A compound represented by formula I:

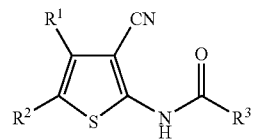

or a pharmaceutically acceptable salt or solvate thereof wherein:

$R^1$ is selected from the group consisting of: H, $C_{1-10}$alkyl, Aryl, Heteroaryl and Heterocyclyl, said alkyl, Aryl, Heteroaryl and Heterocyclyl being optionally substituted with one to four substituents independently selected from $R^6$;

$R^2$ represents $C_{1-10}$alkyl substituted with one to two $R^6$ groups;

$R^3$ is selected from the group consisting of: $C_{1-10}$alkyl and Aryl, said alkyl and Aryl being optionally substituted with one to four substituents independently selected from $R^6$;

each $R^6$ is independently selected from the group consisting of: $OR^7$, Aryl, mono-halophenyl and di-halophenyl.

3. A compound of the formula I:

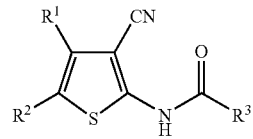

wherein:

$R^1$ represents methyl;

$R^3$ represents 3-pentyl, and $R^2$ is selected from the table below:

| $R^2$ |
|---|

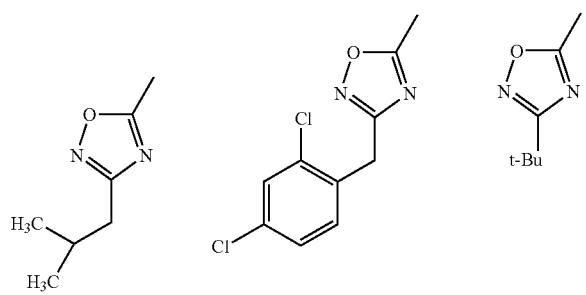

-continued
| R² | | |
|---|---|---|
| 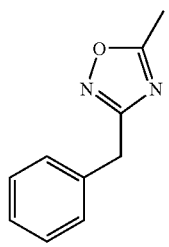 | 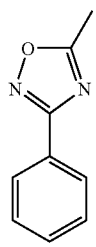 | 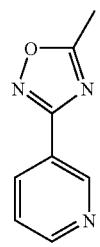 |
| 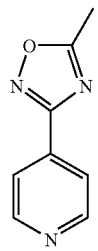 | 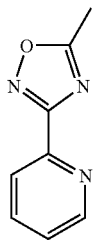 | 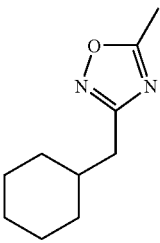 |
| 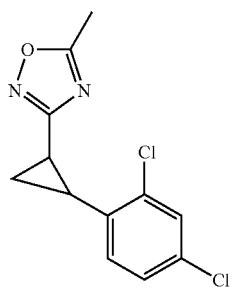 | 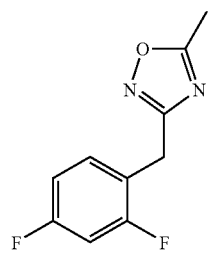 | 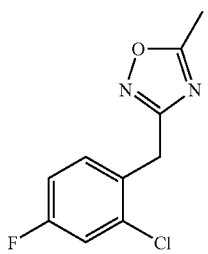 |
| 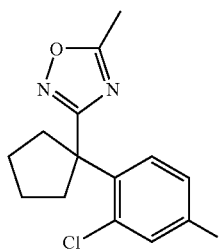 | 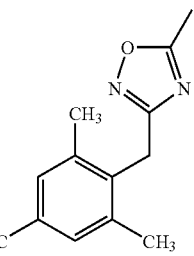 | 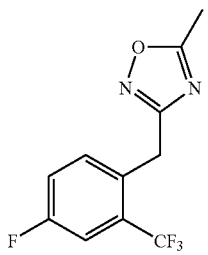 |
| 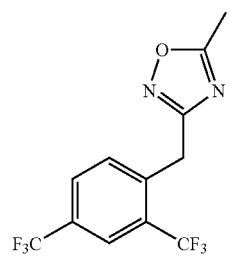 | 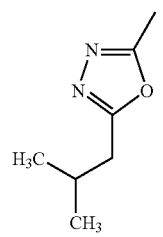 | 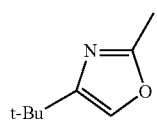 |

-continued
R²
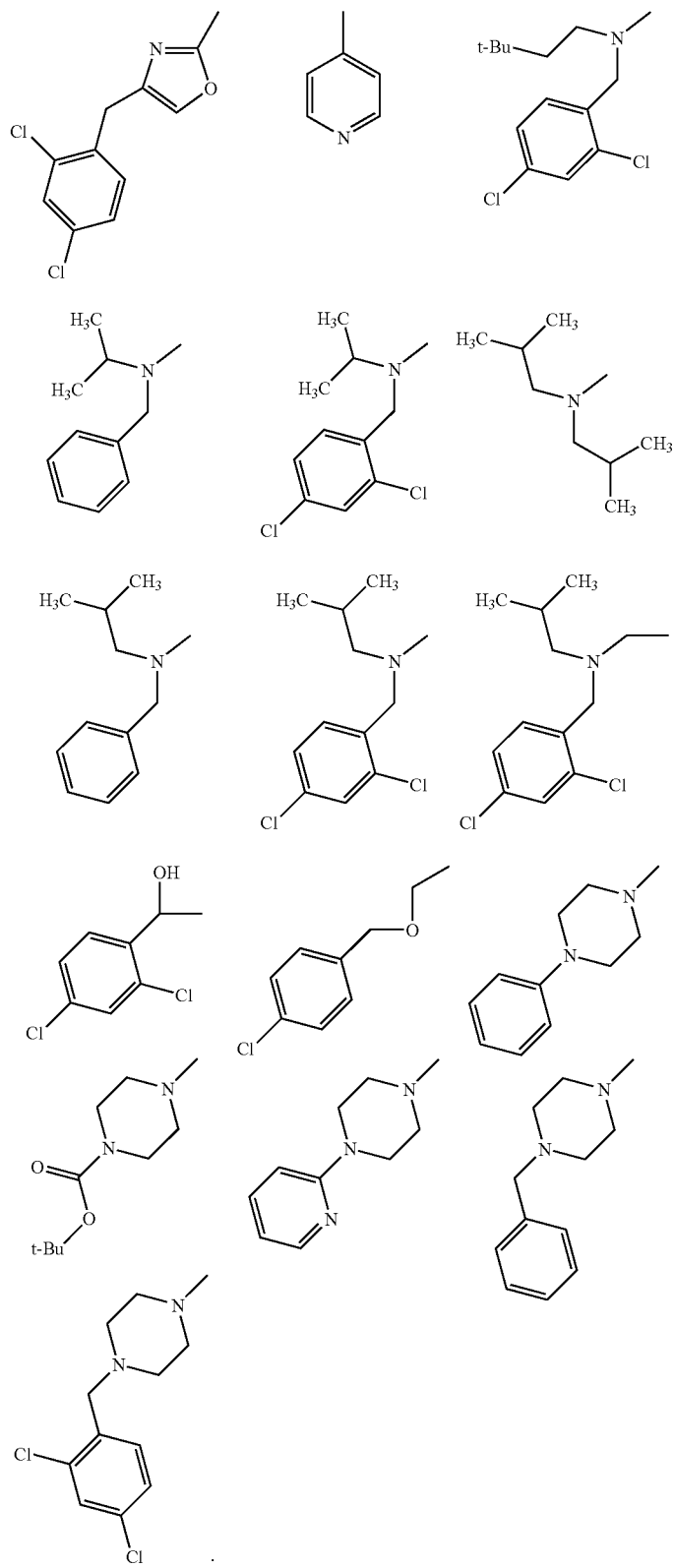

4. A compound selected from the group consisting of:
N-[3-cyano-5-(3-isobutyl-1,2,4-oxadiazol-5-yl)-4-methylthien-2-yl]-2-ethylbutanamide;
N-{3-cyano-5-[3-(2,4-dichlorobenzyl)-1,2,4-oxadiazol-5-yl]-4-methylthien-2-yl}-2-ethylbutanamide;
N-[5-(3-tert-butyl-1,2,4-oxadiazol-5-yl)-3-cyano-4-methylthien-2-yl]-2-ethylbutanamide;
N-[5-(3-benzyl-1,2,4-oxadiazol-5-yl)-3-cyano-4-methylthien-2-yl]-2-ethylbutanamide;
N-[3-cyano-4-methyl-5-(3-phenyl-1,2,4-oxadiazol-5-yl)thien-2-yl]-2-ethylbutanamide;
N-[3-cyano-4-methyl-5-(3-pyridin-2-yl-1,2,4-oxadiazol-5-yl)thien-2-yl]-2-ethylbutanamide;
N-[3-cyano-4-methyl-5-(3-pyridin-3-yl-1,2,4-oxadiazol-5-yl)thien-2-yl]-2-ethylbutanamide;
N-[3-cyano-4-methyl-5-(3-pyridin-4-yl-1,2,4-oxadiazol-5-yl)thien-2-yl]-2-ethylbutanamide;
N-{3-cyano-5-[3-(cyclohexylmethyl)-1,2,4-oxadiazol-5-yl]-4-methylthien-2-yl}-2-ethylbutanamide;
N-(3-cyano-5-{3-[1-(2,4-dichlorophenyl)cyclopropyl]-1,2,4-oxadiazol-5-yl}-4-methylthien-2-yl)-2-ethylbutanamide;
N-{3-cyano-5-[3-(2,4-difluorobenzyl)-1,2,4-oxadiazol-5-yl]-4-methylthien-2-yl}-2-ethylbutanamide;
N-{5-[3-(2-chloro-4-fluorobenzyl)-1,2,4-oxadiazol-5-yl]-3-cyano-4-methylthien-2-yl}-2-ethylbutanamide;
N-(5-{3-[1-(2-chloro-4-fluorophenyl)cyclopentyl]-1,2,4-oxadiazol-5-yl}-3-cyano-4-methylthien-2-yl)-2-ethylbutanamide;
N-{3-cyano-5-[3-(mesitylmethyl)-1,2,4-oxadiazol-5-yl]-4-methylthien-2-yl}-2-ethylbutanamide;
N-(3-cyano-5-{3-[4-fluoro-2-(trifluoromethyl)benzyl]-1,2,4-oxadiazol-5-yl}-4-methylthien-2-yl)-2-ethylbutanamide;
N-(5-{3-[2,4-bis(trifluoromethyl)benzyl]-1,2,4-oxadiazol-5-yl}-3-cyano-4-methylthien-2-yl)-2-ethylbutanamide;
N-[3-cyano-5-(5-isobutyl-1,3,4-oxadiazol-2-yl)-4-methylthien-2-yl]-2-ethylbutanamide;
N-[5-(4-tert-butyl-1,3-oxazol-2-yl)-3-cyano-4-methylthien-2-yl]-2-ethylbutanamide;
N-{3-cyano-5-[4-(2,4-dichlorobenzyl)-1,3-oxazol-2-yl]-4-methylthien-2-yl}-2-ethylbutanamide;
N-(3-cyano-4-methyl-5-pyridin-4-ylthien-2-yl)-2-ethylbutanamide;
N-{3-cyano-5-[(2,4-dichlorobenzyl)(3,3-dimethylbutyl)amino]-4-methylthien-2-yl}-2-ethylbutanamide;
N-{5-[benzyl(isopropyl)amino]-3-cyano-4-methylthien-2-yl}-2-ethylbutanamide;
N-{3-cyano-5-[(2,4-dichlorobenzyl)(isopropyl)amino]-4-methylthien-2-yl}-2-ethylbutanamide;
N-[3-cyano-5-(diisobutylamino)-4-methylthien-2-yl]-2-ethylbutanamide;
N-{5-[benzyl(isobutyl)amino]-3-cyano-4-methylthien-2-yl}-2-ethylbutanamide;
N-{3-cyano-5-[(2,4-dichlorobenzyl)(isobutyl)amino]-4-methylthien-2-yl}-2-ethylbutanamide;
N-{3-cyano-5-[(2,4-dichlorophenyl)(hydroxy)methyl]-4-methylthien-2-yl}-2-ethylbutanamide;
N-(3-cyano-5-{[(2,4-dichlorobenzyl)(isobutyl)amino]methyl}-4-methylthien-2-yl)-2-ethylbutanamide;
N-[3-cyano-4-methyl-5-(4-phenylpiperazin-1-yl)thien-2-yl]-2-ethylbutanamide;
tert-butyl 4-{4-cyano-5-[(2-ethylbutanoyl)amino]-3-methylthien-2-yl}piperazine-1-carboxylate;
N-[3-cyano-4-methyl-5-(4-pyridin-2-ylpiperazin-1-yl)thien-2-yl]-2-ethylbutanamide;
N-[5-(4-benzylpiperazin-1-yl)-3-cyano-4-methylthien-2-yl]-2-ethylbutanamide;
N-{3-cyano-5-[4-(2,4-dichlorobenzyl)piperazin-1-yl]-4-methylthien-2-yl}-2-ethylbutanamide; and
N-(5-{[(4-chlorobenzyl)oxy]methyl}-3-cyano-4-methylthien-2-yl)-2-ethylbutanamide, as well as the pharmaceutically acceptable salts and solvates thereof.

5. A pharmaceutical composition which is comprised of a compound in accordance with claim 1 in combination with a pharmaceutically acceptable carrier.

6. A method of treating type 2 diabetes mellitus in a mammalian patient in need of such treatment, comprising administering to said patient a compound in accordance with claim 1 in an amount that is effective to treat type 2 diabetes mellitus.

7. A method of preventing or delaying the onset of type 2 diabetes mellitus in a mammalian patient in need thereof, comprising administering to said patient a compound in accordance with claim 1 in an amount that is effective to delay the onset of type 2 diabetes mellitus.

8. A method of delaying the onset of type 2 diabetes mellitus in a mammalian patient in need of such treatment, comprising administering to said patient a compound in accordance with claim 2 in an amount that is effective to treat type 2 diabetes mellitus.

9. A method of delaying the onset of type 2 diabetes mellitus in a mammalian patient in need thereof, comprising administering to said patient a compound in accordance with claim 2 in an amount that is effective to delay the onset of type 2 diabetes mellitus.

* * * * *